(12) United States Patent
Fiebig et al.

(10) Patent No.: US 10,028,730 B2
(45) Date of Patent: Jul. 24, 2018

(54) BIOPSY DEVICE TISSUE SAMPLE HOLDER WITH BULK CHAMBER AND PATHOLOGY CHAMBER

(71) Applicant: Devicor Medical Products, Inc., Cincinnati, OH (US)

(72) Inventors: Kevin M. Fiebig, Cincinnati, OH (US); Jessica P. Leimbach, Cincinnati, OH (US); Kyle P. Moore, Woodstock, GA (US); Andrew P. Nock, Dayton, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 53 days.

(21) Appl. No.: 15/079,931

(22) Filed: Mar. 24, 2016

(65) Prior Publication Data

US 2016/0199048 A1    Jul. 14, 2016

Related U.S. Application Data

(62) Division of application No. 13/218,656, filed on Aug. 26, 2011, now Pat. No. 9,326,755.

(51) Int. Cl.
*A61B 10/00* (2006.01)
*A61B 10/02* (2006.01)

(52) U.S. Cl.
CPC ...... *A61B 10/0266* (2013.01); *A61B 10/0096* (2013.01); *A61B 10/0275* (2013.01);
(Continued)

(58) Field of Classification Search
CPC .. A61B 10/06; A61B 10/0266; A61B 10/0275
(Continued)

(56) References Cited

U.S. PATENT DOCUMENTS

| 5,526,822 | A | 6/1996 | Burbank et al. |
| 6,086,544 | A | 7/2000 | Hibner et al. |

(Continued)

FOREIGN PATENT DOCUMENTS

| AU | 2012301511 | | 2/2015 |
| EP | 1642534 | A2 | 4/2006 |

(Continued)

OTHER PUBLICATIONS

Australian Patent Examination Report No. 1 dated Dec. 18, 2013 for Application No. 2012301511, 3 pages.

(Continued)

*Primary Examiner* — Daniel Cerioni
(74) *Attorney, Agent, or Firm* — Frost Brown Todd LLC

(57) ABSTRACT

A biopsy device includes a probe, a holster, and a tissue sample holder for collecting tissue samples. The probe includes a needle and a hollow cutter. The tissue sample holder includes a housing having one or more chambers that are configured to receive a removable tray including one or more prongs and a bulk chamber of a different volume than the one or more chambers. The housing is releasably engageable with the probe. Each tray prong is configured to receive a tissue sample communicated through the cutter lumen. The tray is removable from the housing, such as along an axial direction. The tissue sample holder is rotatable to successively index each chamber to the cutter lumen. The trays may be flexible, resilient, or rigid.

20 Claims, 18 Drawing Sheets

(52) U.S. Cl.
CPC ... *A61B 10/0283* (2013.01); *A61B 2010/0208* (2013.01); *A61B 2010/0225* (2013.01)

(58) Field of Classification Search
USPC .................................................. 600/564
See application file for complete search history.

(56) References Cited

U.S. PATENT DOCUMENTS

| | | |
|---|---|---|
| 6,444,174 B1 | 9/2002 | Lascombes |
| 6,485,436 B1 | 11/2002 | Truckai et al. |
| 6,626,849 B2 | 9/2003 | Huitema et al. |
| 7,442,171 B2 | 10/2008 | Stephens et al. |
| 7,575,556 B2 | 8/2009 | Speeg et al. |
| 7,846,109 B2 | 12/2010 | Parihar et al. |
| 7,854,706 B2 | 12/2010 | Hibner |
| 7,854,707 B2 | 12/2010 | Hibner et al. |
| 7,918,804 B2 | 4/2011 | Monson et al. |
| 7,938,786 B2 | 5/2011 | Ritchie et al. |
| 8,118,755 B2 | 2/2012 | Hibner et al. |
| 8,206,316 B2 | 6/2012 | Hibner et al. |
| 8,251,916 B2 | 8/2012 | Speeg et al. |
| 8,282,574 B2 | 10/2012 | Coonahan et al. |
| 8,328,732 B2 | 12/2012 | Parihar et al. |
| 8,376,957 B2 | 2/2013 | Hibner et al. |
| 8,480,595 B2 | 7/2013 | Speeg et al. |
| 8,485,987 B2 | 7/2013 | Videbaek et al. |
| 8,622,926 B2 | 1/2014 | Hibner |
| 8,622,927 B2 | 1/2014 | Parihar et al. |
| 8,672,860 B2 | 3/2014 | Moore et al. |
| 8,702,623 B2 | 4/2014 | Parihar et al. |
| 8,764,680 B2 | 7/2014 | Rhad et al. |
| 8,858,465 B2 | 10/2014 | Fiebig |
| 8,938,285 B2 | 1/2015 | Fiebig et al. |
| 9,326,755 B2 | 5/2016 | Fiebig et al. |
| 9,345,457 B2 | 5/2016 | Speeg et al. |
| 2005/0131463 A1* | 6/2005 | Fedorov ............. G01N 33/4833 607/2 |
| 2006/0074345 A1 | 4/2006 | Hibner |
| 2008/0195066 A1* | 8/2008 | Speeg ................ A61B 10/0275 604/326 |
| 2008/0200836 A1* | 8/2008 | Speeg ................ A61B 10/0275 600/567 |
| 2009/0131818 A1* | 5/2009 | Speeg ................ A61B 10/0266 600/564 |
| 2009/0209854 A1 | 8/2009 | Parihar et al. |
| 2010/0106053 A1* | 4/2010 | Videbaek .......... A61B 10/0096 600/564 |
| 2010/0152610 A1 | 6/2010 | Parihar et al. |
| 2010/0160816 A1* | 6/2010 | Parihar .............. A61B 10/0275 600/564 |
| 2010/0160819 A1* | 6/2010 | Parihar .............. A61B 10/0275 600/566 |
| 2010/0160824 A1* | 6/2010 | Parihar .............. A61B 10/0096 600/567 |
| 2010/0160826 A1* | 6/2010 | Parihar .............. A61B 10/0275 600/567 |
| 2011/0201964 A1* | 8/2011 | Speeg ................ A61B 10/0275 600/562 |
| 2012/0059247 A1 | 3/2012 | Speeg et al. |
| 2012/0283563 A1* | 11/2012 | Moore .............. A61B 10/0275 600/437 |
| 2013/0041256 A1* | 2/2013 | Fiebig ................ A61B 10/0275 600/432 |

FOREIGN PATENT DOCUMENTS

| | | |
|---|---|---|
| EP | 1932482 A1 | 6/2008 |
| WO | WO 1998/033436 | 8/1998 |
| WO | WO 2000/030531 | 6/2000 |
| WO | WO 2008/076712 | 6/2008 |

OTHER PUBLICATIONS

Australian Patent Examination Report No. 2 dated Sep. 26, 2014 for Application No. 2012301511, 3 pages.
Australian Notice of Acceptance dated Jan. 30, 2015 for Application No. 2012301511, 2 pages.
Australian Patent Examination Report No. 1 dated Apr. 15, 2016 for Application No. 2015202544, 2 pages.
Australian Notice of Acceptance dated Jun. 23, 2016 for Application No. 2015202544, 2 pages.
Chinese First Office Action dated Jan. 6, 2015 for Application No. 201280041497.0, 3 pages.
Chinese Second Office Action dated Sep. 25, 2015 for Application No. 2012800414970, 7 pgs.
Chinese Third Office Action dated Feb. 14, 2016 for Application No. 201280041497.0, 4 pages.
Chinese Fourth Office Action dated Aug. 3, 2016 for Application No. 201280041497.0, 3 pages.
European Extended Search Report dated Apr. 28, 2015 for Application No. 12828656.4, 6 pages.
European Communication dated Aug. 16, 2016 for Application No. 12828656.4, 4 pages.
International Search Report and Written Opinion dated Jan. 3, 2013 for Application No. PCT/US2012/049931.
Japanese First Office Action dated Jun. 28, 2016 for Application No. 2014-527168, 5 pages.

* cited by examiner

BIOPSY DEVICE TISSUE SAMPLE HOLDER WITH BULK CHAMBER AND PATHOLOGY CHAMBER

This application is a divisional of U.S. application Ser. No. 13/218,656, filed Aug. 26, 2011, published as U.S. Pub. No. 2013/0053724 on Jan. 28, 2013, entitled "Biopsy Device Tissue Sample Holder with Bulk Chamber and Pathology Chamber."

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "Mill Compatible Surgical Biopsy Device," issued Sep. 30, 2003; U.S. Pub. No. 2006/0074345, entitled "Biopsy Apparatus and Method," published Apr. 6, 2006; U.S. Pat. No. 7,442,171, entitled "Remote Thumbwheel for a Surgical Biopsy Device," issued Oct. 28, 2008; U.S. Pub. No. 2008/0214955, entitled "Presentation of Biopsy Sample by Biopsy Device," published Sep. 4, 2008; U.S. Pat. No. 7,854,706, entitled "Clutch and Valving System for Tetherless Biopsy Device," issued Dec. 21, 2010; U.S. Pub. No. 2010/0152610, entitled "Hand Actuated Tetherless Biopsy Device with Pistol Grip," published Jun. 17, 2010; U.S. Pub. No. 2010/0160819, entitled "Biopsy Device with Central Thumbwheel," published Jun. 24, 2010; U.S. Pub. No. 2010/0160824, entitled "Biopsy Device with Discrete Tissue Chambers," published Jun. 24, 2010; U.S. Pub. No. 2010/0317997, entitled "Tetherless Biopsy Device with Reusable Portion," published Dec. 16, 2010; U.S. Non-Provisional patent application Ser. No. 12/953,715, entitled "Handheld Biopsy Device with Needle Firing," filed Nov. 24, 2010; and U.S. Non-Provisional patent application Ser. No. 13/086,567, entitled "Biopsy Device with Motorized Needle Firing," filed Apr. 14, 2011. The disclosure of each of the above-cited U.S. Patents, U.S. Patent Application Publications, and U.S. Non-Provisional Patent Applications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
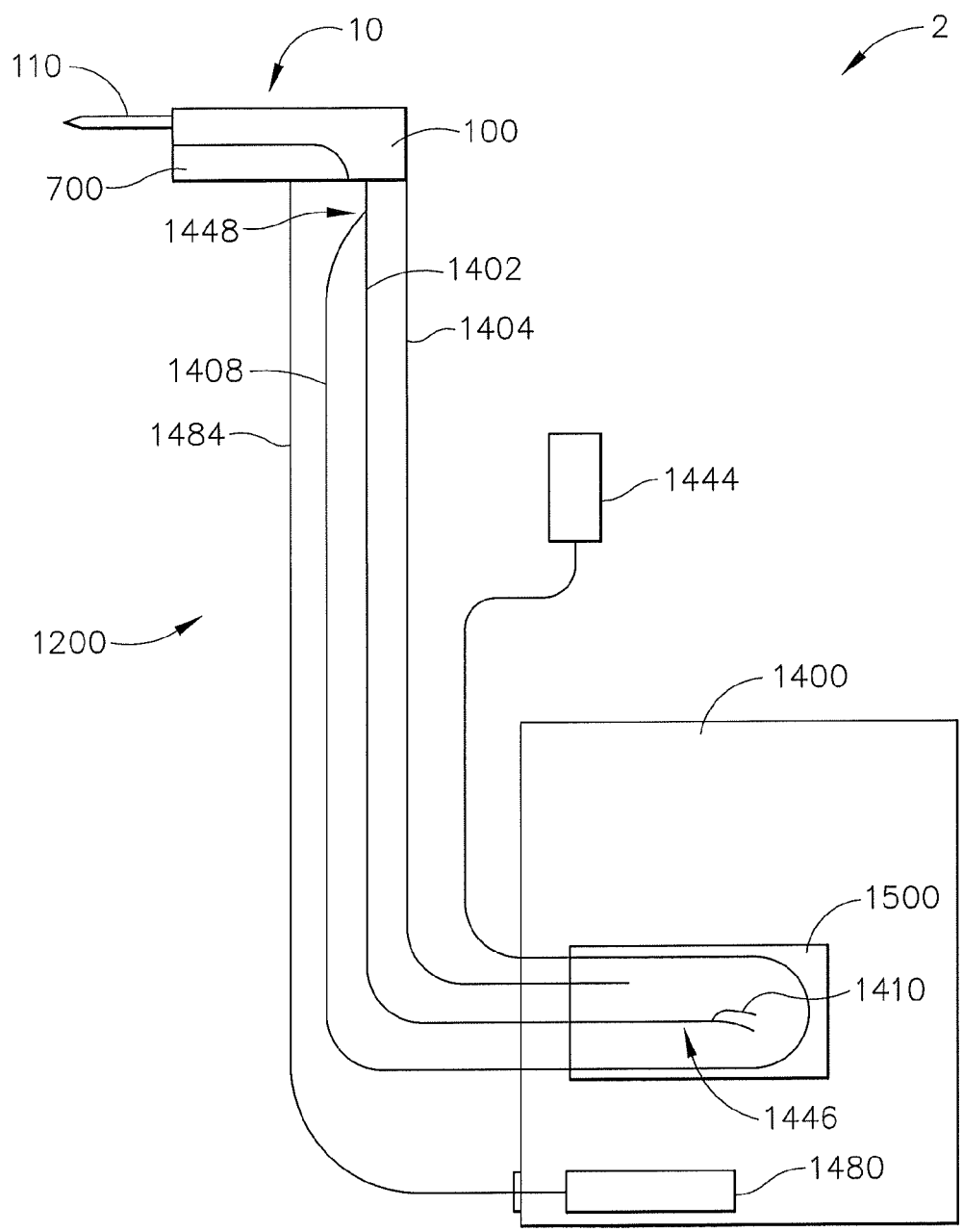
FIG. 1 is a schematic view of an exemplary biopsy system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device

Figure 3:
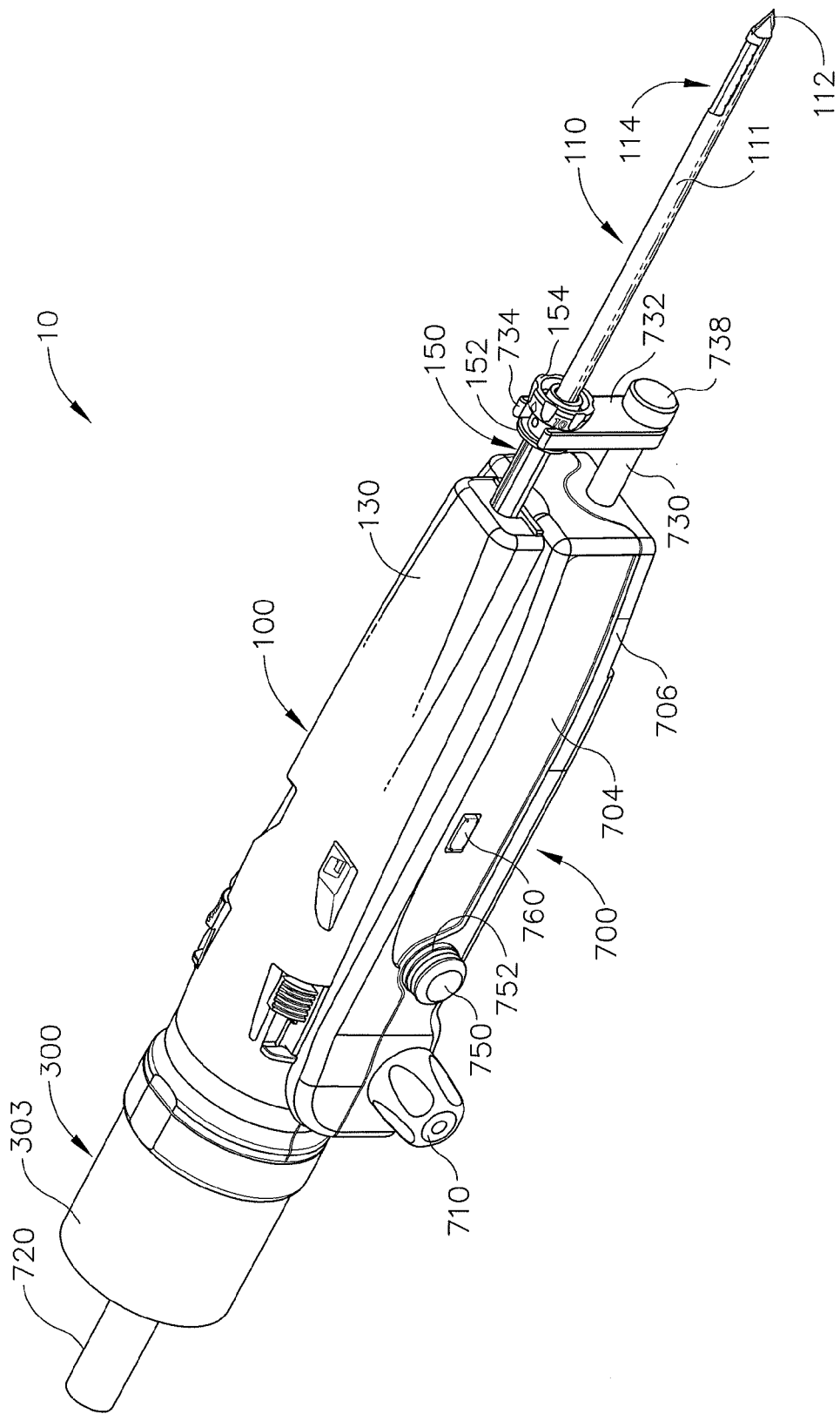
FIG. 3 is a perspective view of a holster and a probe of an exemplary biopsy device coupled together, the probe including a tissue sample holder.
Figure 4:
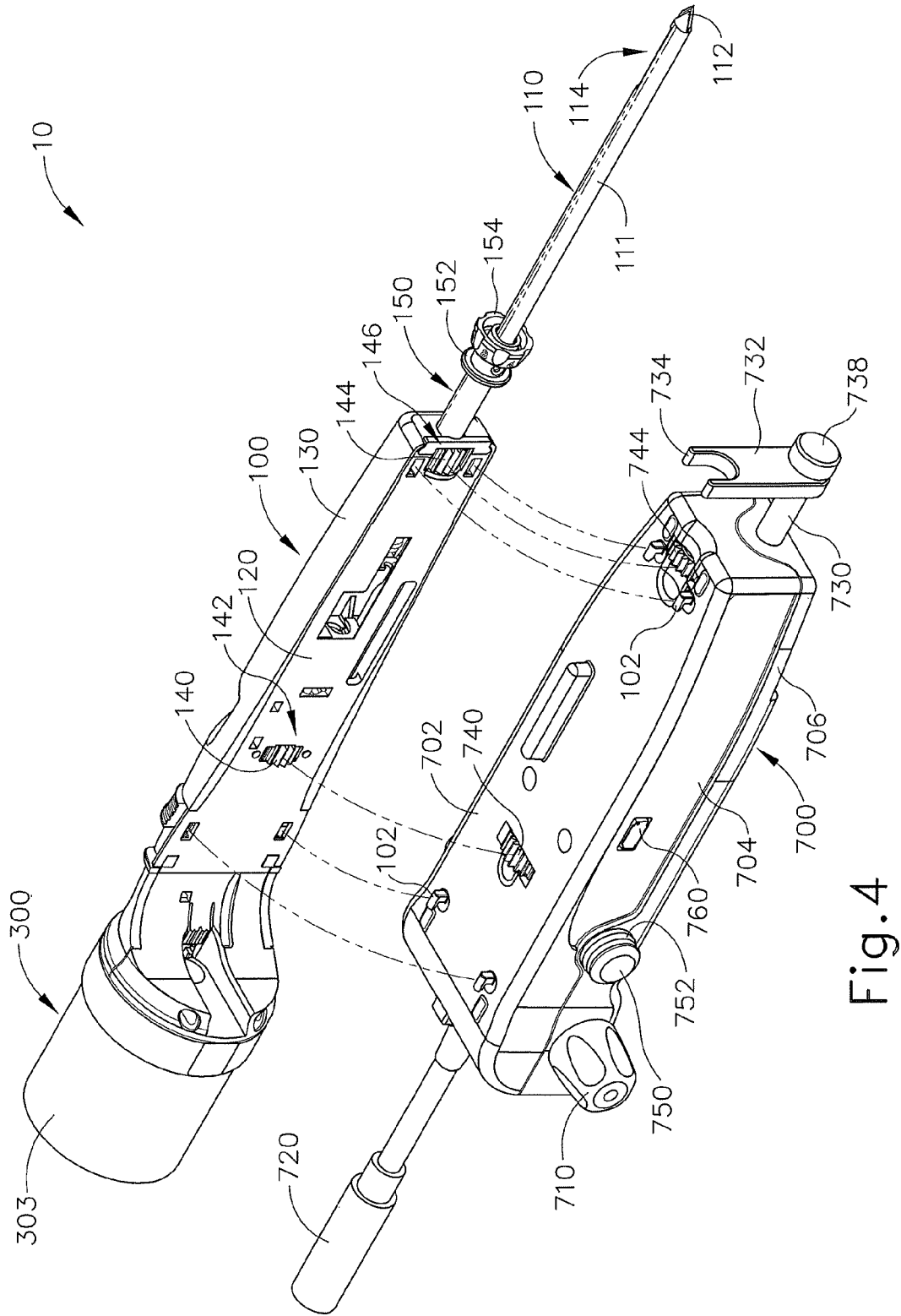
FIG. 4 is a perspective view of the biopsy device of FIG. 3, showing the probe separated from the holster to expose an underside of the probe and a top side of the holster.

As shown in FIG. 1, an exemplary biopsy system (2) includes a biopsy device (10) and a vacuum control module (1400). As shown in FIGS. 3-4, biopsy device (10) comprises a probe (100), a holster (700), and a tissue sample holder (300). As will be described in greater detail below and as shown in FIG. 4, probe (100) is separable from its corresponding holster (700).

By way of example only, probe (100) may be provided as a disposable component, while holster (700) may be provided as a reusable component. Vacuum control module (1400) is provided on a cart (not shown) in the present example, though like other components described herein, a cart is merely optional. A control module interface (not shown) may also be provided between biopsy device (10) and vacuum control module (1400), for providing electrical and mechanical communication to biopsy device (10); as well as electrical communication with vacuum control module (1400). By way of example only, control module (1400) may be constructed and operable in accordance with at least some of the teachings of U.S. Patent App. Publ. No. 2008/0214955, entitled "Presentation of Biopsy Sample by Biopsy Device", published Sep. 4, 2008, the disclosure of which is incorporated by reference herein. Among other components described herein, a footswitch (not shown) and/or other devices may be used to provide at least some degree of control of at least a portion of biopsy system (2). As shown in FIG. 1, conduits (1200) provide communication of power (e.g., mechanical such as through a cable, electrical, pneumatic, etc.), control signals, saline, vacuum, and venting from vacuum control module (1400) to biopsy device (10). Each of these components will be described in greater detail below.

Figure 2:
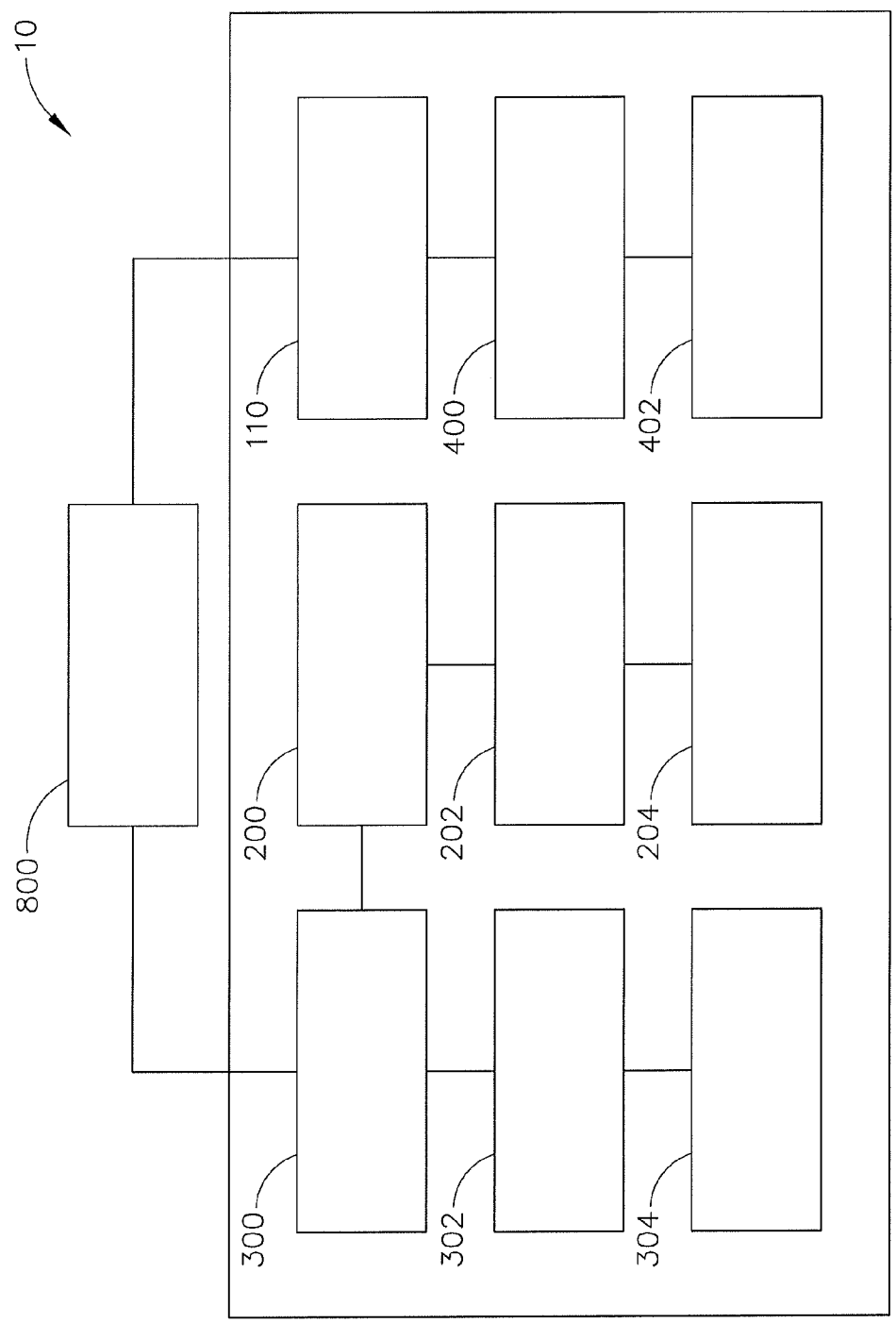
FIG. 2 is a block schematic diagram showing various components of an exemplary biopsy device.

FIGS. 2-4 show an exemplary biopsy device (10). As described above, biopsy device (10) of this example comprises a probe (100) and a holster (700). Referring to FIGS. 3-4, a needle (110) extends distally from probe (100), and is inserted into a patient's tissue to obtain tissue samples as will be described in greater detail below. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (700). While prongs (102) are used to removably secure probe (100) to holster (700) in the present example, as shown in FIG. 4, it should be understood that a variety of other types of structures, components, features, etc. (e.g., bayonet mounts, latches, clamps, clips, snap fittings, etc.) may be used to provide removable coupling of probe (100) and holster (700). Furthermore, in some biopsy devices (10), probe (100) and holster (700) may be of unitary or integral construction, such that the two components cannot be separated. By way of example only, in versions where probe (100) and holster (700) are provided as separable components, probe (100) may be provided as a disposable component, while holster (700) may be provided as a reusable component. Still other suitable structural and functional relationships between probe (100) and holster (700) will be apparent to those of ordinary skill in the art in view of the teachings herein.

Some variations of biopsy device (10) may include one or more sensors (not shown), in probe (100) and/or in holster (700), that is/are configured to detect when probe (100) is coupled with holster (700). Such sensors or other features may further be configured to permit only certain types of probes (100) and holsters (700) to be coupled together. In addition or in the alternative, such sensors may be configured to disable one or more functions of probes (100) and/or holsters (700) until a suitable probe (100) and holster (700) are coupled together. Of course, such sensors and features may be varied or omitted as desired.

In some versions as shown in FIG. 2, biopsy device (10) includes a vacuum source (800), such as a vacuum pump. By way of example only, vacuum source (800) may be incorporated into probe (100), incorporated into holster (700), and/or be a separate component altogether. In versions where vacuum source (800) is separate from probe (100) and holster (700), vacuum source (800) may be coupled with probe (100) and/or holster (700) via one or more conduits such as flexible tubing (1402, 1408) (shown in the example of FIG. 1 as vacuum control module (1400) and conduit (1200) and as described in detail further below). As shown in FIG. 2, vacuum source (800) is in fluid communication with tissue sample holder (300) and needle (110). Thus, vacuum source (800) may be activated to draw tissue into lateral aperture (114) of needle portion or needle (110). Tissue sample holder (300) is also in fluid communication with cutter (200). Vacuum source (800) may thus also be activated to draw severed tissue samples through the hollow interior of cutter (200) and into tissue sample holder (300). Other suitable ways in which vacuum source (800) may be used will be apparent to those of ordinary skill in the art in view of the teachings herein. It should also be understood that vacuum source (800) may simply be omitted, if desired.

In some versions, vacuum source (800) is provided in accordance with the teachings of U.S. Pub. No. 2008/0214955, the disclosure of which was incorporated by reference above. In addition or in the alternative, vacuum source (800) may be provided in accordance with the teachings of U.S. Non-Provisional patent application Ser. No. 12/953,715, the disclosure of which is incorporated by reference above. As yet another merely illustrative example, vacuum source (800) may be provided in accordance with the teachings of U.S. Non-Provisional patent application Ser. No. 12/709,695, entitled "Biopsy Device with Auxiliary Vacuum Source," filed Feb. 22, 2010, the disclosure of which is incorporated by reference herein. Still other suitable ways in which vacuum source (800) may be provided will be apparent to those of ordinary skill in the art in view of the teachings herein.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

As shown in FIG. 1, an exemplary vacuum canister (1500) is configured to be coupled with vacuum control module (1400). Vacuum control module (1400) is operable to induce a vacuum through vacuum canister (1500), and such a vacuum may be communicated to biopsy probe (100). For instance, vacuum control module (1400) may communicate a vacuum through tube (1404), which may then communicate the vacuum through tissue sample holder (300) to a cutter lumen (not shown) of probe 100 as described below. Vacuum control module (1400) may also communicate a vacuum through tube (1402) to a manifold of hub member or hub (150), as shown in FIGS. 3-4, which may then communicate the vacuum to a vacuum lumen (not shown) of outer cannula (111) of needle 110.

Furthermore, vacuum canister (1500) is operable to collect fluids that are communicated from biopsy probe (100) during use of biopsy probe (100). Vacuum canister (1500) may thus be regarded as providing a fluid interface between biopsy probe (100) and vacuum control module (1400). Any suitable vacuum control module and vacuum canister may be used such as those described in U.S. Pub. 2008/0214955, entitled "Presentation of Biopsy Sample by Biopsy Device," published Sep. 4, 2008 and U.S. Pub. No. 2010/0160824, entitled "Biopsy Device with Discrete Tissue Chambers", published Jun. 24, 2010, the disclosures of which are incorporated by reference herein. Further, any other suitable component, system, technique, or device may be used with the suitable control module or vacuum canister.

As shown in FIG. 1, a tube (1408) is fed into tube (1402). Tube (1410) is also fed into tube (1402). In particular, a connector (1446) connects saline tube (1408) with tube (1402). As shown, connector (1446) is provided adjacent to canister (1500), while connector (1448) is provided near biopsy probe (100). In the present example, connectors (1446, 1448) simply provide a constantly open conduit between tubes (1410, 1402) and tubes (1408, 1402), respectively. In some other versions, connectors (1446, 1448) may have any other suitable components (e.g., valve, etc.). It will be appreciated in view of the disclosure herein that the configuration of tubes (1402, 1408, 1410) and connectors (1446, 1448) permits any of a vacuum, vent, or saline to be communicated through tube 1402). An exemplary determination of which of these will be communicated through tube (1402) will be described in greater detail below. As also shown, saline bag (1444) is coupled with tube (1408) using any suitable conventional fitting.

Vacuum control module (1400) of the present example may also include a controller (1480) operable to control motors in holster (700). By way of example only, control module (1400) may be constructed and operable in accordance with at least some of the teachings of U.S. Pat. No. 7,938,786, entitled "Vacuum Timing Algorithm for Biopsy Device", issued May 10, 2011, the disclosure of which is incorporated by reference herein. Other suitable ways in which vacuum, saline, other fluids, and/or control may be provided will be apparent to those of ordinary skill in the art in view of the teachings herein.

II. Exemplary Probe

As shown in FIGS. 2-4, probe (100) of the present example includes a distally extending needle (110). Probe (100) also includes a chassis (120) and a top housing (130), which are fixedly secured together. As best seen in FIG. 4, a gear (140) is exposed through an opening (142) in chassis (120), and is operable to drive cutter actuation mechanism (202) (FIG. 2) in probe (100). As also seen in FIG. 4, another gear (144) is exposed through another opening (146) in chassis (120), and is operable to rotate needle (110). Gear (140) of probe (100) meshes with exposed gear (740) of holster (700) when probe (100) and holster (700) are coupled together. Similarly, gear (144) of probe (100) meshes with exposed gear (744) of holster (700) when probe (100) and holster (700) are coupled together.

As will be explained in more detail below, tissue sample holder (300) is removably secured to a rear member of probe (100), though tissue sample holder (300) may alternatively be secured to some other component of probe (100). As described above, though not shown in FIGS. 2-4, a pair of tubes (1402, 1404) is coupled with probe (100) for providing fluid communication therewith.

Suitable configurations for probe (100) will be apparent to those of ordinary skill in the art in view of the teachings herein. For instance, probe (100) may be configured in accordance with any of the teachings in U.S. Patent App. Pub. No. 2008/0214955, entitled "Presentation of Biopsy Sample by Biopsy Device," published Sep. 4, 2008, the disclosure of which is incorporated by reference herein. Other ways in which probe (100) may be configured are disclosed in U.S. Patent App. Pub. No. 2010/0160816, entitled "Mechanical Tissue Sample Holder Indexing Device," published Jun. 24, 2010, the disclosure of which is incorporated by reference herein; U.S. Patent App. Pub. No. 2010/0160821, entitled "Biopsy Device With Sliding Cutter Cover," published Jun. 24, 2010, the disclosure of which is incorporated by reference herein; U.S. Patent App. Pub. No. 2010/0160819, entitled "Biopsy Device With Central Thumbwheel," published Jun. 24, 2010, the disclosure of which is incorporated by reference herein; U.S. Non-Provisional patent application Ser. No. 13/086,567, entitled "Biopsy Device with Motorized Needle Firing," filed Apr. 14, 2011, the disclosure of which is incorporated by reference herein; and/or U.S. Pub. No. 2010/0160824, entitled "Biopsy Device with Discrete Tissue Chambers," published Jun. 24, 2010, the disclosure of which is incorporated by reference herein. Still other ways in which probe (100) may be formed, including alternative techniques, materials, and configurations, will be apparent to those of ordinary skill in the art in view of the teachings herein.

A. Exemplary Needle

Needle (110) of the present example includes a piercing tip (112), a lateral aperture (114) located proximal to tip (112), and a hub member (150). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. Tip (112) may also be configured to provide greater echogenicity than other portions of needle (110), providing enhanced visibility of tip (112) under ultrasound imaging. By way of example only, tip (112) may be configured in accordance with any of the teachings in U.S. Non-Provisional patent application Ser. No. 12/875,200, entitled "Echogenic Needle for Biopsy Device," filed Sep. 3, 2010, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (200) having a sharp distal edge (not shown) is located within needle (110). Cutter (200) is operable to rotate and translate relative to needle (110) and past lateral aperture (114) to sever a tissue sample from tissue protruding through lateral aperture (114). For instance, cutter (200) may be moved from an extended position to a retracted position, thereby "opening" lateral aperture (114) to allow tissue to protrude therethrough; then from the retracted position back to the extended position to sever the protruding tissue. While lateral aperture (114) is shown oriented in an upward position in FIG. 3, it should be understood that needle (110) may be rotated to orient lateral aperture (114) at any desired angular position about the longitudinal axis of needle (110). Such rotation of needle (110) is facilitated in the present example by hub member (150).

Hub member (150) of the present example is overmolded about needle (110), such that hub member (150) and needle (110) rotate and translate unitarily with each other. By way of example only, needle (110) may be formed of metal, and hub member (150) may be formed of a plastic material that is overmolded about needle (110) to unitarily secure and form hub member (150) to needle (110). Hub member (150) and needle (110) may alternatively be formed of any other suitable material(s), and may be secured together in any other suitable fashion. Hub member (150) includes an annular flange (152) and a thumbwheel (154). Gear (144) is slidably and coaxially disposed on a proximal portion (150) of hub member (150) and is keyed to hub member (150), such that rotation of gear (144) will rotate hub member (150) and needle (110); yet hub member (150) and needle (110) may translate relative to gear (144). Gear (144) is rotatably driven by gear (744). Alternatively, needle (110) may be rotated by rotating thumbwheel (154). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein. Needle (110) may be translated longitudinally relative to chassis (120) and top housing (130), particularly by a needle firing mechanism (400) (FIG. 2), for example.

It should be understood that, as with other components described herein, needle (110) may be varied, modified, substituted, or supplemented in a variety of ways; and that needle (110) may have a variety of alternative features, components, configurations, and functionalities. A plurality of external openings (not shown) may also be formed in needle (110), and may be in fluid communication with a lumen (not shown). For instance, such external openings may be configured in accordance with the teachings of U.S. Pat. No. 7,918,804, entitled "Biopsy Device with Vacuum Assisted Bleeding Control," issued Apr. 5, 2011, the disclosure of which is incorporated by reference herein. Cutter (200) may also include one or more side openings (not shown). Of course, as with other components described herein, such external openings in needle (110) and cutter (200) are merely optional. As yet another merely illustrative example, needle (110) may be constructed and operable in accordance with the teachings of U.S. Patent App. Pub. No. 2008/0214955, entitled "Presentation of Biopsy Sample by Biopsy Device," published Sep. 4, 2008, the disclosure of which is incorporated by reference herein, and/or in accordance with the teachings of any other reference cited herein.

Probe (100) may also include a valve assembly in fluid communication with at least part of needle (110), selectively changing a pneumatic state of at least part of needle (110) based on any suitable conditions such as the longitudinal position of cutter (200). By way of example only, such a valve assembly may be constructed and operable in accordance with the teachings of U.S. Pub. No. 2010/0317997, entitled "Tetherless Biopsy Device with Reusable Portion," published Dec. 16, 2010, the disclosure of which is incorporated by reference herein, and in accordance with the teachings of U.S. Non-Provisional patent application Ser. No. 12/953,715, entitled "Handheld Biopsy Device with Needle Firing," filed Nov. 24, 2010, the disclosure of which is incorporated by reference herein, or otherwise. In addition or in the alternative, valving may be provided by vacuum source (800) (FIG. 2) and/or a vacuum canister, such as is taught in U.S. Patent App. Pub. No. 2008/0214955, entitled "Presentation of Biopsy Sample by Biopsy Device," published Sep. 4, 2008, the disclosure of which is incorporated by reference herein. Other suitable alternative versions, features, components, configurations, and functionalities of needle (110) will be apparent to those of ordinary skill in the art in view of the teachings herein.

B. Exemplary Cutter Actuation Mechanism

As noted above, cutter (200) is operable to rotate and translate relative to needle (110) and past lateral aperture (114) to sever a tissue sample from tissue protruding through lateral aperture (114). This action of cutter (200) is provided by a cutter actuation mechanism (202). Cutter actuation mechanism (202) is positioned mainly in probe (100) in the present example, though it should be understood that cutter actuation mechanism (202) may be positioned mainly in holster (700) and/or both in probe (100) and holster (700). Cutter actuation mechanism (202) includes meshing gears (140, 740), with gear (740) being driven by motor (204). Motor (204) is located in holster (700) in the present example, though it should be understood that motor (204) may alternatively be located in probe (100) and/or elsewhere.

By way of example only, cutter actuation mechanism (202) may be constructed and operable in accordance with the teachings of U.S. Patent App. Pub. No. 2008/0214955, the disclosure of which was incorporated by reference above. As another merely illustrative example, cutter actuation mechanism (202) may be constructed and operable in accordance with the teachings of U.S. Pub. No. 2010/0317997, the disclosure of which was incorporated by reference above. As yet another merely illustrative example, cutter actuation mechanism (202) may be constructed and operable in accordance with the teachings of U.S. Patent App. Pub. No. 2010/0292607, entitled "Tetherless Biopsy Device with Self-Reversing Cutter Drive Mechanism," published Nov. 18, 2010, the disclosure of which is incorporated by reference herein. Alternatively, cutter actuation mechanism (202) may be constructed in accordance with the teachings of any other reference cited herein. It should also be understood that biopsy device (10) may be configured such that cutter (200) does not translate (e.g., such that cutter (200) merely rotates, etc.); or such that cutter (200) does not rotate (e.g., such that cutter (200) merely translates, etc.). As another merely illustrative example, cutter (200) may be actuated pneumatically in addition to or in lieu of being actuated by mechanical components. Other suitable alternative versions, features, components, configurations, and functionalities of cutter actuation mechanism (202) will be apparent to those of ordinary skill in the art in view of the teachings herein.

C. Exemplary Cutter

A hollow cutter (200) is disposed within a cannula lumen of outer cannula (111) in the present example. The interior of cutter (200) defines a cutter lumen, such that fluid and tissue may be communicated through cutter (200) via the cutter lumen. As will be described in greater detail below, cutter (200) is configured to rotate within the cannula lumen of outer cannula (111) and translate axially within the cannula lumen of outer cannula (111). In particular, cutter (200) is configured to sever a biopsy sample from tissue protruding through transverse aperture (114) of outer cannula (111). As will also be described in greater detail below, cutter (200) is further configured to permit severed tissue samples to be communicated proximally through the cutter lumen. Merely illustrative examples of such severing and proximal communication are described in U.S. Pat. No. 5,526,822, entitled "Method and Apparatus for Automated Biopsy and Collection of Soft Tissue," issued Jun. 18, 1996, the disclosure of which is incorporated by reference herein, though any other suitable structures or techniques may be used for severing and/or communicating tissue samples within a biopsy system (2). Still other ways in which cutter (200) may be configured or treated, including alternative techniques and materials, will be apparent to those of ordinary skill in the art in view of the teachings herein.

D. Exemplary Tissue Sample Holder

Tissue sample holder (300) of the present example, described in greater detail below, comprises an outer cup (303) and a rotatable manifold or inner housing (304) that includes a plurality of chambers configured to receive tissue samples that are severed by cutter (200) and communicated proximally through the hollow interior of cutter (200). Tissue sample holder (300) also includes one or more removable trays that permit a user to remove severed tissue samples from tissue sample holder (300) without having to remove tissue sample holder (300) from chassis (120). Tissue sample holder (130) may further include an inner housing or rotatable manifold, as described in detail below, that is in fluid communication with vacuum source (800) and cutter (200) and that is rotatable to successively index the chambers to cutter (200). In particular, the manifold is rotated by a tissue sample holder rotation mechanism (302), which is driven by a motor (301). It should be understood that at least part of tissue sample holder rotation mechanism (302) and/or motor (301) may be incorporated into probe (100), into holster (700), or into both probe (100) and holster (700). It should also be understood that some versions of tissue sample holder (300) may be driven manually, pneumatically, or otherwise.

By way of example only, tissue sample holder (300) may be constructed and operable in accordance with the teachings of U.S. Pub. No. 2008/0214955, the disclosure of which was incorporated by reference above. As another merely illustrative example, tissue sample holder (300) may be constructed and operable in accordance with the teachings of U.S. Pub. No. 2010/0160824, entitled "Biopsy Device with Discrete Tissue Chambers," published Jun. 24, 2010, the disclosure of which is incorporated by reference herein. As yet another merely illustrative example, tissue sample holder (300) may be constructed an operable in accordance with the teachings of U.S. Pub. No. 2008/0221480, entitled "Biopsy Sample Storage," published Sep. 11, 2008, the disclosure of which is incorporated by reference herein.

Outer cup (303) of the examples disclosed herein has a cylindrical shape defining a distal end and a proximal end, though any other suitable shapes or configurations may be used. Outer cup (303) is configured to engage probe (100) in a bayonet fashion, such that outer cup (303) may be selectively removed from or secured to probe (100). More specifically, the distal end of outer cup (303) includes a plurality of slots (305) capable of engaging protrusions (not shown) of probe (100) upon sufficient rotation of outer cup (303) relative to probe (100). Other suitable configurations for providing selective engagement between outer cup (303) and probe (100) will be apparent to those skilled in the art in view of the teachings herein. Additionally, cup (303) remains stationary while housing (304) rotates within cup (303). Cup (303) may also provide additional sealing for tissue sample holder (302) as a whole. It should be understood, however, that like other components described herein, cup (303) is merely optional and may be omitted or varied in a number of ways if desired. Still other suitable ways in which tissue sample holder (300) may be constructed and operable will be apparent to those of ordinary skill in the art in view of the teachings herein.

III. Exemplary Holster

As shown in FIGS. 3-4, holster (700) of the present example includes a top housing cover (702), side panels (704), and a housing base (706), which are fixedly secured together. As best seen in FIG. 4 and as noted above, gears (740, 744) are exposed through top housing cover (702), and mesh with gears (140, 144) of probe (100) when probe (100) and holster (120) are coupled together. In particular, gears (740, 140) drive cutter actuation mechanism (202); while gears (744, 144) are employed to rotate needle (110). Holster (700) also includes a firing rod (730) and fork (732), which couple with needle (110) and fire needle (110) distally as will be described in greater detail below.

All motors (204, 304, 402) referred to herein are contained within holster (700) in the present example and receive power from an external source via cable (720). In addition or in the alternative, data may be communicated via cable (720) from holster (700) and/or to holster (700) as desired. In some other versions, motors (204, 304, 402) are powered by one or more batteries located within holster (700) and/or probe (100). It should therefore be understood that, as with other components described herein, cable (720) is merely optional. As yet another merely illustrative variation, motors (204, 304, 402) may be powered pneumatically, such that cable (720) may be substituted with a conduit communicating a pressurized fluid medium to holster (700). As still other merely illustrative variation, cable (720) may include one or more rotary drive cables that are driven by motors (204, 304, 402) that are located external to holster (700). It should also be understood that two or three of motors (204, 304, 402) may be combined as a single motor. Other suitable ways in which various mechanisms (202, 302, 400) may be driven will be apparent to those of ordinary skill in the art in view of the teachings herein.

A. Exemplary Needle Rotation Mechanism

As noted above, rotation of gear (744) provides rotation of needle (110) relative to probe (100). In the present example, gear (744) is rotated by rotating knob (710). In particular, knob (710) is coupled with gear (744) by a series of gears (not shown) and shafts (not shown), such that rotation of knob (710) rotates gear (744). A second knob (710) extends from the other side of holster (700). By way of example only, such a needle rotation mechanism may be constructed in accordance with the teachings of U.S. Pub. No. 2008/0214955, the disclosure of which is incorporated by reference herein. As another merely illustrative example, a needle rotation mechanism may be constructed in accordance with the teachings of U.S. Pub. No. 2010/0160819, the disclosure of which was incorporated by reference above. In some other versions, needle (110) is rotated by a motor. In still other versions, needle (110) is simply rotated by rotating thumbwheel (154). Various other suitable ways in which rotation of needle (110) may be provided will be apparent to those of ordinary skill in the art in view of the teachings herein. It should also be understood that some versions may provide no rotation of needle (110).

B. Exemplary Needle Firing Mechanism

Holster (700) of the present example further includes a needle firing mechanism (400), which is operable to fire needle (110) from a loaded position. By way of example only, such firing may be useful in instances where biopsy device (10) is mounted to a stereotactic table fixture or other fixture, with tip (112) adjacent to a patient's breast, such that needle firing mechanism (400) may be activated to drive needle (110) into the patient's breast. Needle firing mechanism (400) may be configured to drive needle (110) along any suitable range of motion, to drive tip (112) to any suitable distance relative to fixed components of probe (100). Needle firing mechanism (400) of the present example is activated by activation buttons (760) and arming buttons (750). Activation buttons (760) comprise thin film switches presented on side panels (704) of holster (700). In some versions activations buttons (760) are on both sides of holster (700) while in other versions activation buttons (760) are either on just one side of holster (700) or are located elsewhere (e.g., remote user interface, at vacuum source (800) or elsewhere, etc.). Activation buttons (760) are operable to selectively activate motor (402) to load needle firing mechanism (400). Arming buttons (750) are also provided on both sides of holster (700) in the present example, and are mechanically movable transversely relative to side panels (704). Each arming button (750) includes a bellows (752) that provides a fluid tight seal with side panel (704). Of course, either type of button (750, 760) may have various other components, features, configurations, and operabilities.

In the present example, needle firing mechanism (400) is coupled with needle (110) via a firing rod (732) and a firing fork (732). Firing rod (732) and firing fork (734) are unitarily secured together by complementary flats and a pin (738). Firing fork (732) includes a pair of prongs (734) that receive hub member (150) of needle (110) therebetween. Prongs (734) are positioned between annular flange (152) and thumbwheel (154), such that needle (110) will translate unitarily with firing rod (730) and fork (732). Prongs (734) nevertheless removably receive hub member (150), such that fork (732) may be readily secured to hub member (150) when probe (100) is coupled with holster (700); and such that hub member (150) may be readily removed from fork (732) when probe (100) is decoupled from holster (700). Prongs (734) are also configured to permit hub member (150) to rotate between prongs (734), such as when knob (710) is rotated to change the angular orientation of lateral aperture (114). Other suitable components, configurations, and relationships will be apparent to those of ordinary skill in the art in view of the teachings herein. By way of example only, needle firing mechanism (400) may be constructed and operable in accordance with at least some of the teachings of U.S. Non-Provisional patent application Ser. No. 13/086, 567, entitled "Biopsy Device with Motorized Needle Firing," filed Apr. 14, 2011, the disclosure of which is incorporated by reference herein. Various other suitable ways in which needle firing mechanism (400) may be fired will be apparent to those of ordinary skill in the art in view of the teachings herein. It should also be understood that some versions may provide no firing of needle (110).

IV. Exemplary First Version of an Inner Housing for a Tissue Sample Holder

Figure 5:
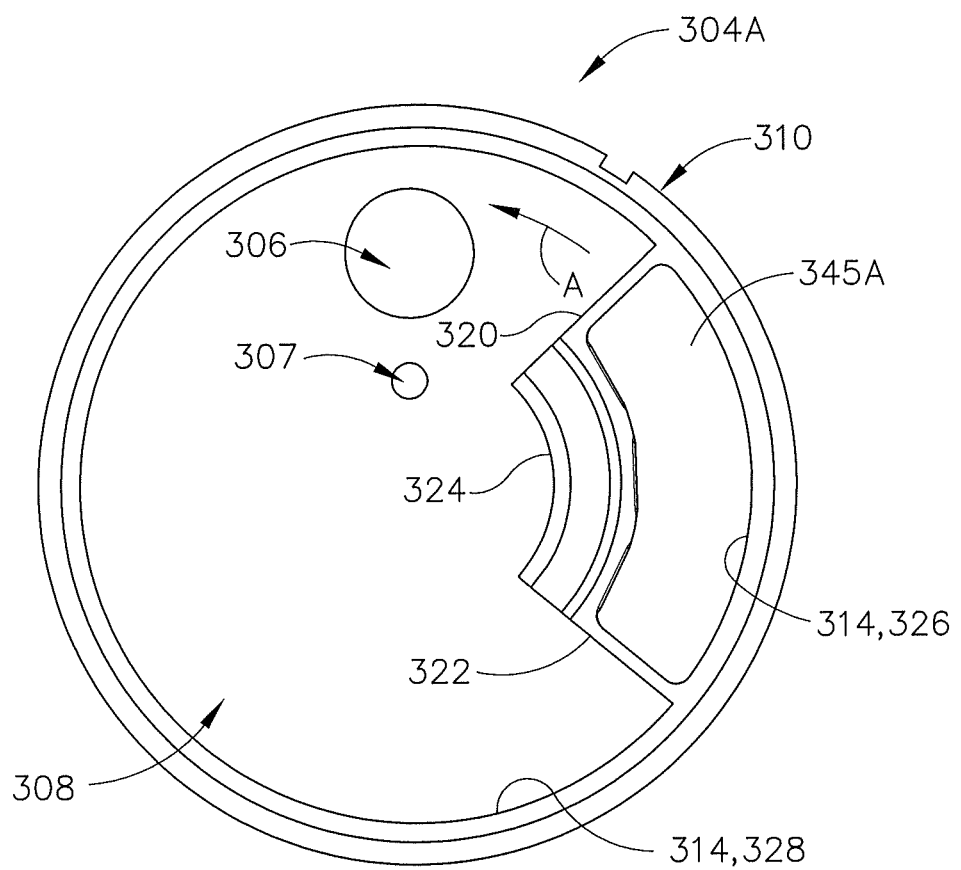
FIG. 5 is an end view of an example of an inner housing for the tissue sample holder of FIG. 3 attached to an end of the probe of FIG. 3, showing a tissue sample entry point of the probe, a bulk chamber within the inner housing, and a tray receiving chamber within the inner housing.

FIGS. 5-8 show an exemplary first version of an internal or inner housing (304A) of tissue sample holder (300) of biopsy device (10). FIG. 5 shows exemplary inner housing (304A) as including bulk chamber (308), and tray receiving/tissue sample chamber (345A). Exemplary inner housing (304A) is positioned over a tissue sample entry point or port (306), which is disposed at a distal end of probe (100), through which a tissue sample may be received. FIG. 5 also shows a vacuum port (307), which is disposed at a distal end of probe (100). Inner housing (304A) is in fluid communication with vacuum source (800) via vacuum port (307). Vacuum is communicated through port (307) from vacuum source (800), then through tissue ample holder (300) to port (306). Such communication allows tissue to be drawn through a lumen of cutter (200), through exit port (306), and then into tissue sample holder (300).

Inner housing (304A) is rotatable within outer cup (303) of tissue sample holder (300) to index tissue sample chamber (345A) or bulk chamber (308) with port (306) and cutter (200). Additionally or alternatively, outer cup (303) may be omitted, and inner housing (304A) may be manually or automatically rotated to index tissue sample chamber (345A) with cutter (200). For example, rotation may be effected by motor (301) via a gear shaft, such as shaft (422) (see FIG. 13), connectable to intermeshing gears in probe (100) and holster (700) for operation by the motor, disposed in probe (100) and/or holster (700). Rotation of other examples inner housings of the present disclosure may be effected in a similar manner.

As an example of rotation, tissue sample chamber (345A) of FIG. 5 may be rotated along the direction of arrow (A), as well as in an opposite direction, to be disposed over port (306) such that one or more tissue samples may be received within tissue sample chamber (345A). Alternatively, tissue sample chamber (345A) of FIG. 5 may be rotated to a position in which tissue sample chamber (345A) is not disposed over port (306) such that one or more tissue samples are then received within bulk chamber (308) via port (306). Vacuum port (307) of probe (100) may include a filter or a screen to prevent tissue from clogging vacuum port (307) when bulk chamber (308) is indexed to port (306). In addition or in the alternative, probe (100) may include or communicate with a pressure pump to provide a positive air pressure through vacuum port (307) to clear debris from vacuum port (307) and/or to clear a filter/screen positioned at vacuum port (307). It should also be understood that cup (303) may include a sump feature for removal of excess fluid, etc.

Figure 6:
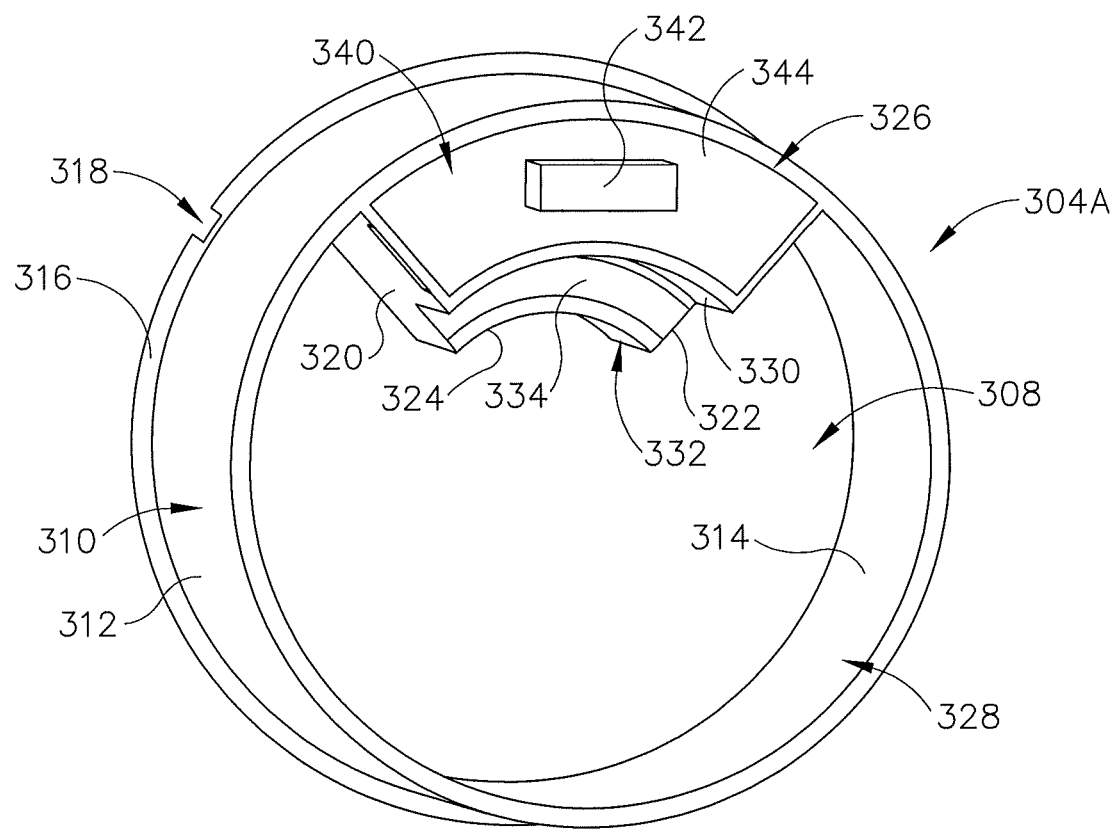
FIG. 6 is a perspective view of the proximal end of the inner housing of FIG. 5 and a removable tray that is received in the tray receiving chamber of FIG. 5.

Referring to FIG. 6, inner housing (304A) includes outer annular wall (310) including exterior wall face (312), interior wall face (314), and outer annular ridge (316) projecting transversely from outer annular wall (310). Outer annular ridge (316) includes internal walls defining notch (318), which is shown in this example to have a square shape but may include other shapes, such as circular or triangular shapes or combinations thereof. Further, while ridge (316) is shown to include a single notch (318), ridge (316) may include multiple notches (318) of similar or differing shapes and/or sizes. Notch (318) may receive a corresponding protrusion of the rotation assisting member of probe (100) described above, for example, to assist with the rotation of inner housing (304A) with respect to probe (100) and/or holster (700).

Figure 7:
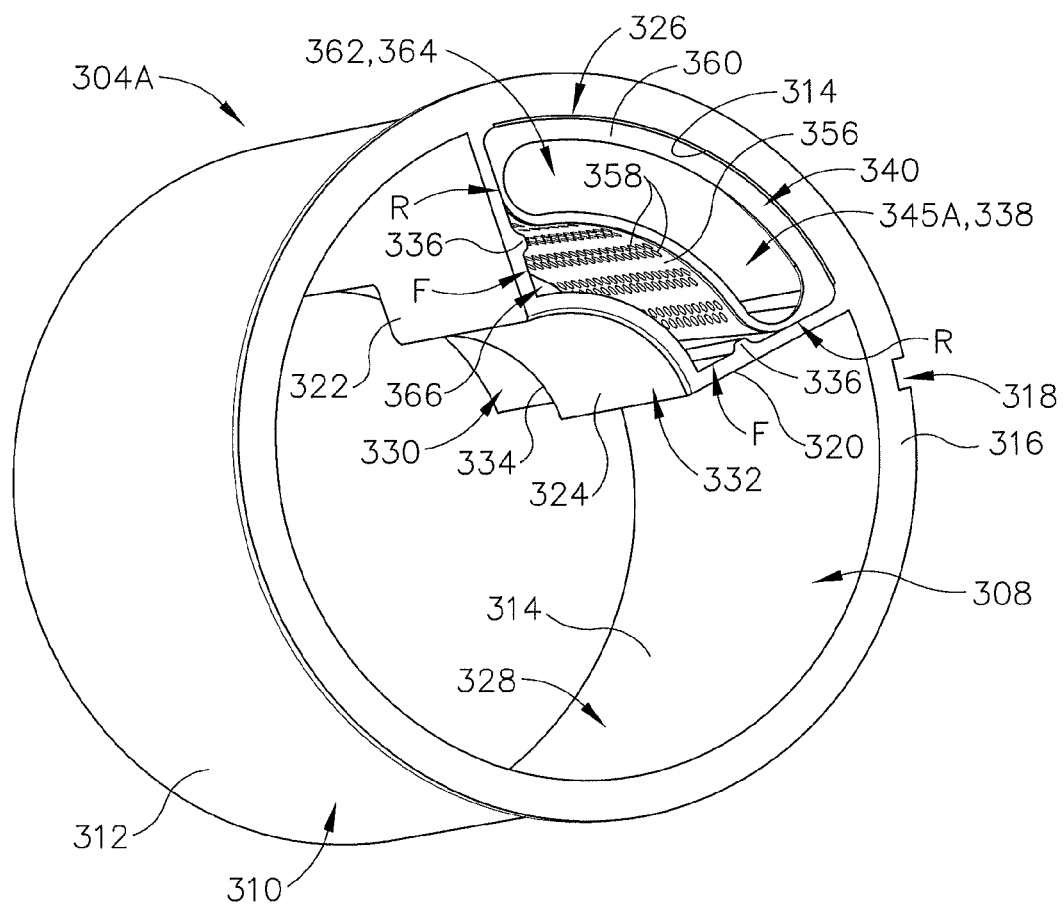
FIG. 7 is a perspective view of the distal end of the inner housing and removable tray of FIG. 6.

Inner housing (304A) includes tissue sample chamber (345A) and bulk chamber (308), which are separated by walls (320, 322, 324). As shown in FIG. 7, interior faces of walls (320, 322, 324) face towards first portion (326) of interior wall face (314) of outer annular wall (310) and, with first portion (326), define tissue sample chamber (345A). Exterior faces of walls (320, 322, 324) face towards second portion (328) of interior wall face (314) of outer annular wall (310) and, with second portion (328), define bulk chamber (308).

Figure 12:
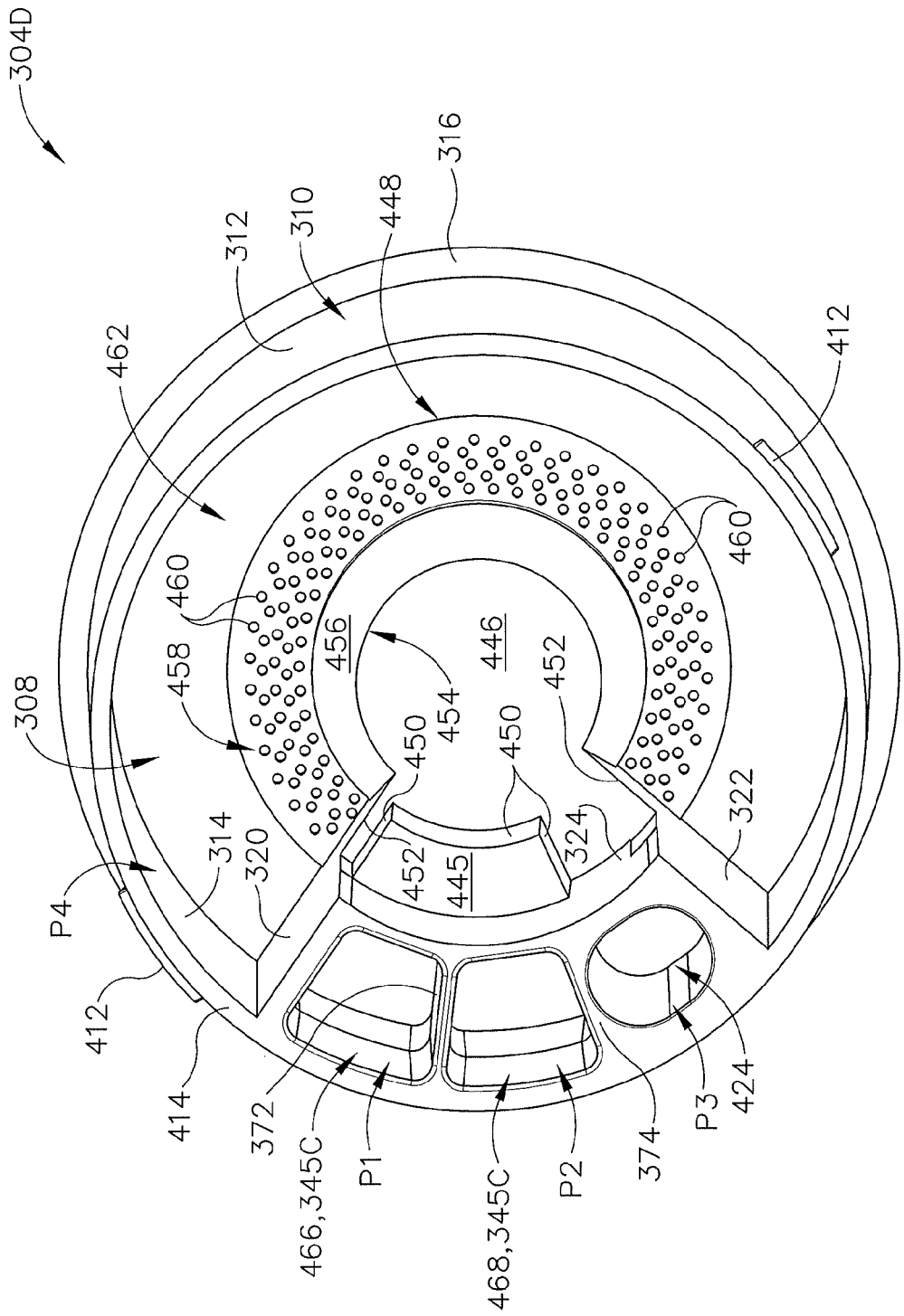
FIG. 12 is a perspective view of the proximal end of another example of an inner housing for the tissue sample holder of FIG. 3.

Walls (320, 322) project inwardly from interior wall face (314) of outer annular wall (310) of inner housing (304A), and wall (324) is disposed between end portions of walls (320, 322). While wall (324) is shown as an arcuately shaped inner member, wall (324) may be formed to include any other suitable sizes and shapes. Alternatively, wall (324) may be omitted such that walls (320, 322) meet at a point and form a triangular shape, as shown in FIG. 12 in a variation that is discussed in greater detail below.

In the present example, each of walls (320, 322, 324) include an upper, proximal portion and a lower, distal portion. Upper, proximal portion (330) of centrally disposed wall (324) is separated from lower, distal portion (332) of wall (324) by ledge (334). Lower, distal portions of inwardly projecting walls (320, 322) have a width that is greater than the width of upper, proximal portions of walls (320, 322) by the distance that upper and lower portions of centrally disposed wall (324) are separated by ledge (334).

Figure 8:
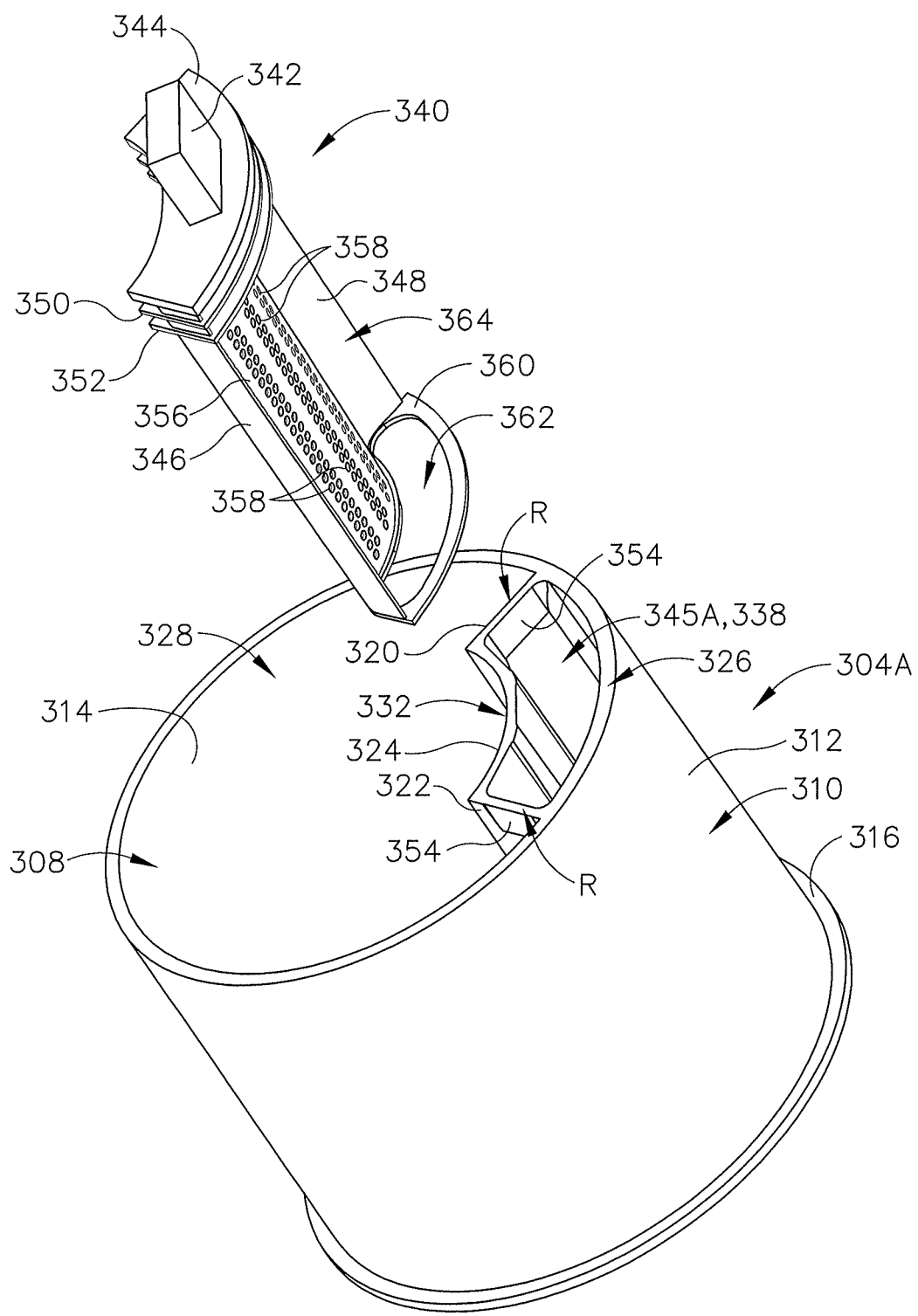
FIG. 8 is an exploded perspective view of the inner housing and removable tray of FIG. 6.

Referring to FIG. 7, interior faces of inwardly projecting walls (320, 322) each include front portion (F), rear portion (R), and a longitudinally extending protrusion (336). In the example shown in FIG. 7, protrusions (336) internally extend from the upper portion of each of walls (320, 324). Protrusions may alternatively or additionally extend from other walls described within the scope of this disclosure. Elongated protrusions (336), rear portions (R) of the interior faces of walls (320, 322), and interior wall face (314) of outer annular wall (310) define a distal end of tray space (338) for receiving and retaining removable tray (340). As shown in FIG. 8, the rear portions of the interior faces of walls (320, 322), interior wall face (314) of outer annular wall (310), and the interior face of the upper portion of centrally disposed wall (324) together define a proximal end of tray space (338) to receive removable tray (340).

Tray (340), as shown in FIG. 8, includes handle (342) proximally extending from arcuate and elongate proximal end wall (344), which has a proximal edge and a distal edge. Handle (342) may assist a user with inserting or removing tray (340) from tray space (338); and with manually rotating inner housing (304A) when tray (340) is received within tray space (338). Sidewalls or outer tray walls (346, 348), having proximal and distal edges, project distally from an underside or distal edge of proximal end wall (344). Elongate arcuate walls (350, 352) are disposed below and proximate to proximal end wall (344) and have substantially the same shape as proximal end wall (344). Peripheral ends of proximal end wall (344) and elongate arcuate walls (350, 352) act as wiper seals providing an additional seal between the proximal end of tray (340) and tissue sample chamber (345A) when tray (340) is received in tray space (338) of tissue sample chamber (345A) to prevent potential seepage of tissue sample fluid or the tissue sample; and also help to maintain a vacuum within chamber (345A). The peripheral ends may, for example, form a frictional fit with the walls defining tray space (338) of inner housing (304A). Tray (340) and/or other components of tissue sample holder (300) may also include face seals and/or various types of elastomers to create a seal. Additionally or alternatively, peripheral opposite side ends of one or more of walls (344, 350, 352) may be received with apertures (354) defined in a proximal portion of walls (320, 322).

Arcuately shaped floor (356) is disposed between outer tray walls (346, 348) and includes apertures (358). At a distal end, base end wall (360) extends from floor (356) and is disposed between ends of outer tray wall (346, 348). Base end wall (360) is sized for reception within tray space (338). Base end wall (360) defines aperture (362) through which a tissue sample may be received from, for example, cutter (200) via port (306) as described above. Floor (356), outer tray walls (346, 348), an underside of wall (352), and base end wall (360) define tissue sample receiving space (364). Apertures (358) of arcuately shaped floor (356) may be of any suitable shape and size. For example, apertures (358) may have a circular shape and be sized large enough such that fluids from a tissue sample received in tissue sample receiving space (364) may flow through apertures (358) to fluid receiving space (366) while the tissue sample remains in tray (340) positioned within tray space (338). Fluid receiving space (366) is formed, as shown in FIG. 7, by front portions of the interior face of walls (320, 322), elongate protrusions (336), an underside of ledge (334), the interior face of the distal portion of centrally disposed wall (324), and floor (356) of tray (340). Fluid receiving space (366) is disposed over vacuum port (307) of probe (100) when housing (304A) is rotated to position tissue sample chamber (345A) over port (306). The fluid may then flow back through biopsy device (10) through to tubes connected to vacuum source (800).

In use, an initial set of tissue samples may be received and piled into bulk chamber (308), disposed over and aligned with port (306) of probe (100). Inner housing (304A) with bulk chamber (308) disposed over port (306) may be automatically indexed, via motor (301) as described above, for example, after each receipt of a tissue sample through port (306). Eventually, inner housing (304A) will be indexed to a point at which tissue sample chamber (345A) will be disposed over and aligned with port (306), instead of a portion of bulk chamber (308), to receive a tissue sample. At this point, after a first set of tissue samples are received in bulk chamber (308), the sample received in tissue sample chamber (345A) may be treated as a pathological sample for lab testing purposes, for example, and the samples received in bulk chamber (308) may be discarded. A similar use may occur in and for any of the inner housing examples of the present disclosure, in which samples received within tissue sample chambers may be pathological samples for further testing (such as an oncology sample stored in formalin prior to testing) and samples received in bulk chamber (308) may be discarded.

V. Exemplary Second Version of an Inner Housing for a Tissue Sample Holder

Figure 9:
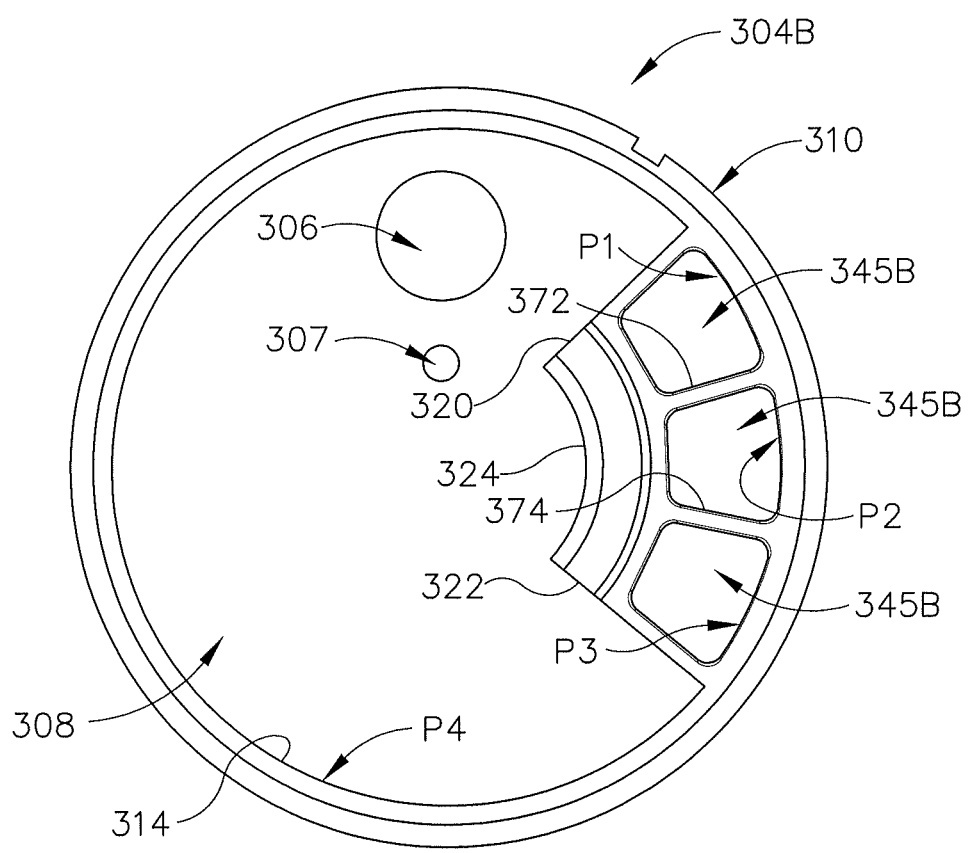
FIG. 9 is an end view of another example of an inner housing for the tissue sample holder of FIG. 3 attached to an end of the probe of FIG. 3, showing a tissue sample entry point of the probe, a bulk chamber within the inner housing, and tray receiving chambers within the inner housing.
Figure 10:
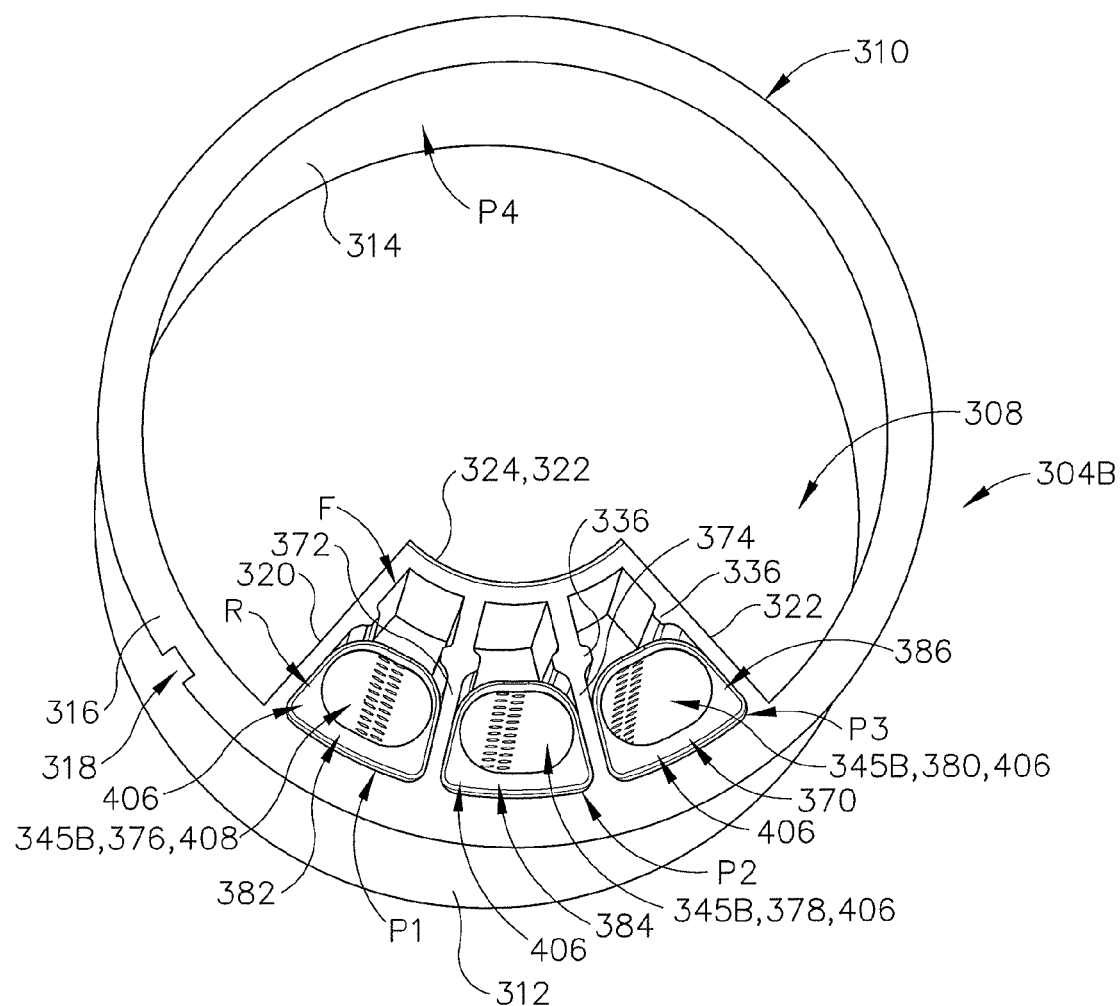
FIG. 10 is a perspective view of the distal end of the inner housing of FIG. 9 and a removable tray that is received within the tray receiving chambers of FIG. 9.
Figure 11:
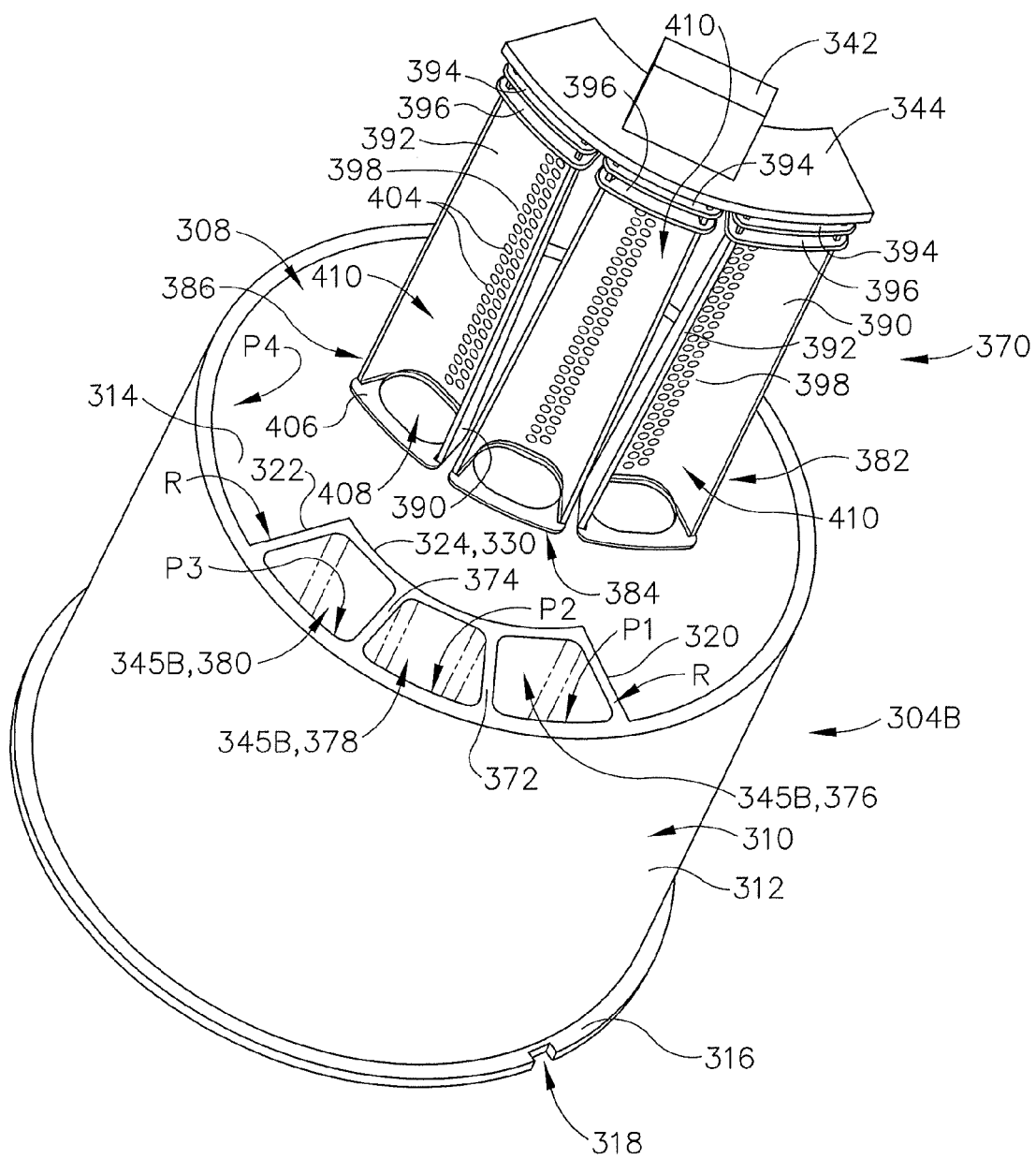
FIG. 11 is an exploded perspective view of the inner housing and removable tray of FIG. 10.

FIGS. 9-11 show another exemplary version of inner housing (304B) for tissue sample holder (300) of biopsy device (10). Exemplary inner housing (304B) is positioned over port (306), as described above for inner housing (304A). The reference numbers used for like components of inner housing (304A) are also used for inner housing (304B). Further, the similarities between the versions herein will generally not be further discussed. When tray (370) is received in tray spaces of inner housing (304B), the proximal end view is similar to the proximal end view shown in FIG. 6 for inner housing (304A). From a distal view of inner housing (304B), however, or when tray (370) is not received within the tray spaces of inner housing (304B), the inner housing (304B) differs from inner housing (304A) in that it includes three tissue sample chambers (345B) rather than just one such chamber (345A). Inner housing (304B) also includes a bulk chamber (308). Tissue sample chambers (345B) are separated from bulk chamber (308) by walls (320, 322, 324). Walls (320, 322) project inwardly from interior wall face (314) of outer annular wall (310) of inner housing (304A), and wall (324) is disposed between end portions of walls (320, 322). While wall (324) is shown as arcuately shaped, wall (324) may be formed to include other shapes apparent to those of ordinary skill in the art.

The second version of inner housing (304B) of tissue sample holder (300) further includes interior walls (372, 374) disposed between inwardly extending walls (320, 322) and extending between interior wall face (314) of outer annular wall (310) and centrally disposed wall (324) to define three tissue sample chambers (345B). While three such chambers are shown in this example, more or fewer interior walls may be included to define a greater or fewer number of chambers, respectively. Interior faces of walls (320), (324) and interior wall (372) along with first portion (P1) of interior wall face (314) of outer annular wall (310) define a first tissue sample chamber (345B). An opposite face of interior wall (372), an interior face of centrally disposed wall (324), and a face of interior wall (374), along with second portion (P2) of interior wall face (314), define a second tissue sample chamber (345B). An opposite face of interior wall (374), interior faces of walls (322, 324), and third portion (P3) of interior wall face (314) define a third tissue sample chamber (345B). Exterior faces of walls (320, 322, 324) face towards fourth portion (P4) of interior wall face (314) and, with the fourth portion, define bulk chamber (308).

As shown in FIG. 10 and similar to the first version, interior faces of inwardly projecting walls (320, 322) as well as the faces of interior walls (372, 374) each include front portion (F), rear portion (R), and an elongated protrusion (336) internally extending from the upper portion of each of the walls. Elongated protrusions (336), the rear portions of walls (320, 322, 372, 374), and interior wall face (314) of outer annular wall (310) together define a distal end of three separate tray space cavities (376, 378, 380) for receiving and retaining three respective prongs (382, 384, 386) of removable tray (370), respectively, as described below. As shown in FIG. 11, the rear portions of walls (320, 322, 372, 374), first, second, and third portions (P1, P2, P3) of interior wall face (314) of outer annular wall (310), and the interior face of the upper portion of centrally disposed wall (324) together define a proximal end of tray space cavities (376, 378, 380) to respectively receive prongs (382, 384, 386) of removable tray (370).

Tray (370), as shown in FIG. 11, includes handle (342) proximally extending from arcuate and elongate proximal end wall (344). Outer tray walls (390, 392) of first prong (382), outer tray walls (390, 392) of second prong (384), and outer tray walls (390, 392) of third prong (386) each project distally from an underside of proximal end wall (344). A pair of arcuate walls (394, 396) is disposed distal and proximate to proximal end wall (344) for each of the prongs. External peripheral ends of proximal end wall (344) and arcuate walls (394, 396) act as wiper seals providing an additional seal between the proximal end of tray (370) and tissue sample chambers (345B) when the three prongs (382, 384, 386) of tray (370) are respectively received in tray space cavities (376, 378, 380) defined by walls of tissue sample chambers (345B) to prevent potential seepage of tissue sample liquid or the tissue sample; and also help to maintain a vacuum within chambers (345B). The peripheral ends may, for example, form a frictional fit with the walls of tray space cavities (376, 378, 380) of inner housing (304A). Tray (370) and/or other components of tissue sample holder (300) may also include face seals and/or various types of elastomers to create a seal.

Floors (398) are disposed between each set of outer tray walls (390, 392) and include apertures (404). At a distal end, each of the prongs includes base end wall (406) extending from a respective floor (398). Each base end wall (406) is disposed between ends of respective outer tray walls (390, 392). Base end walls (406) are each sized for reception within respective tray space cavities (376, 378, 380). Base end walls (406) each include internal walls defining aperture (408) through which a tissue sample may be received from, for example, cutter (200) as described above. For each prong, floor (398), outer tray walls (390, 392), an underside of wall (396), and base end wall (406) define a tissue sample receiving space (410). Apertures (408) of arcuately shaped floor (398) are sized in a manner similar to that described above for the first version.

In use, inner housing (304B) may be indexed in a manner similar to inner housing (304A) such that bulk chamber (308) may initially be disposed over port (306) of probe (100) to receive tissue samples and inner housing (304B) may be indexed after each such receipt until one of tissue sample chambers (345B) receive a tissue sample. Further, indexing may continue until each of tissue sample chambers (345B) have received a respective tissue sample for potential pathological uses, such as use as an oncology sample stored in formalin prior to testing, while tissue samples received in bulk chamber (308) may be discarded. Such auto-indexing toward and receipt into multiple tissue sample chambers is possible for the inner housing examples disclosed herein that include multiple tissue sample chambers.

VI. Exemplary Third Version of an Inner Housing for a Tissue Sample Holder

Figure 13:
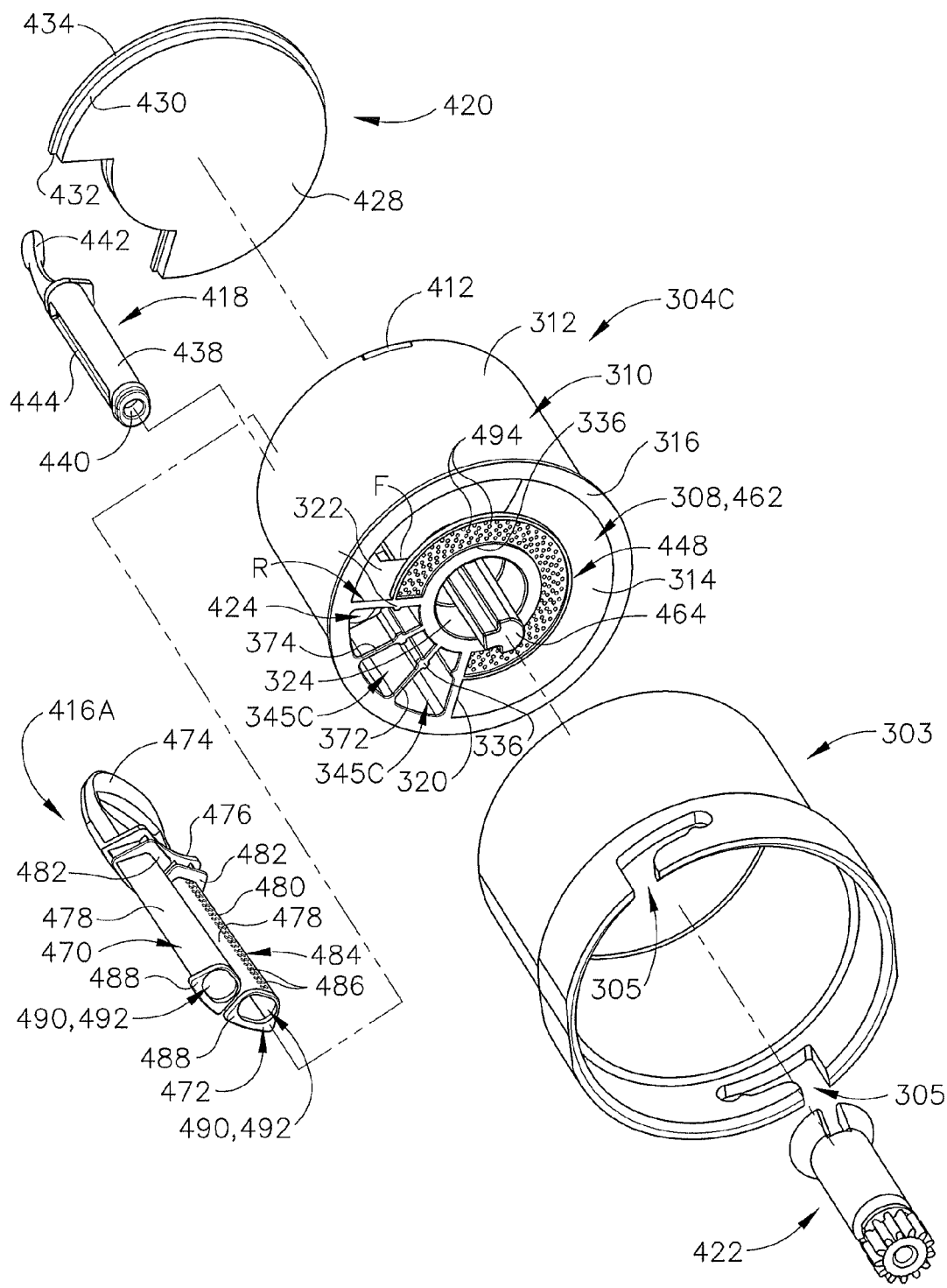
FIG. 13 is an exploded view of the tissue sample holder of FIG. 3, showing the inner housing of FIG. 12, a two-prong tray, a marker and/or medication seal plug, a bulk chamber cap, a gear shaft, and an outer cup.
Figure 14:
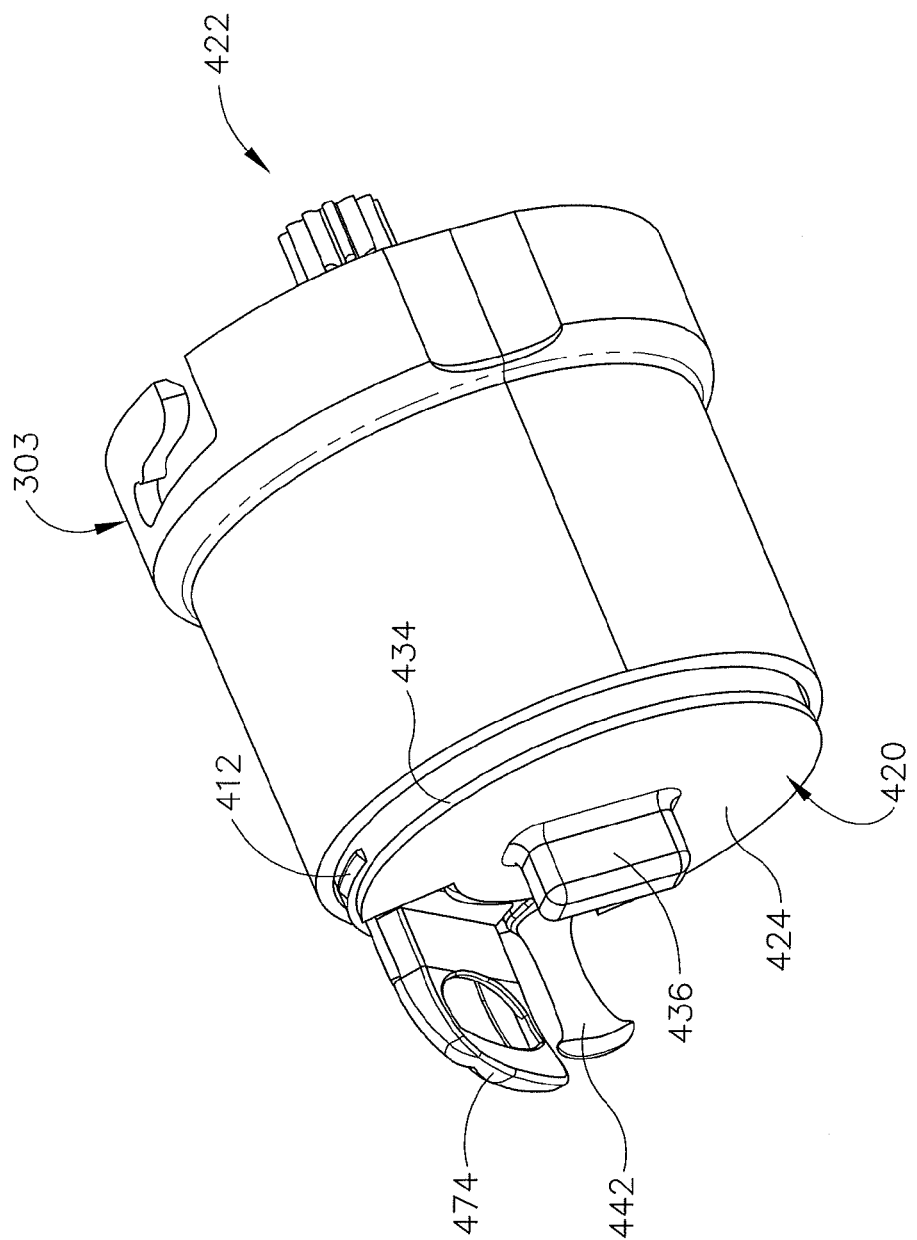
FIG. 14 is a perspective, assembled view of the tissue sample holder of FIG. 13.

FIGS. 12-14 show another exemplary version of inner housing (304C) for tissue sample holder (300) of biopsy device (10). The reference numbers used for like components of inner housings (304A, 304B) are also used for inner housing (304C). Further, the similarities between the versions will generally not be further discussed.

Referring to FIG. 12, a proximal view of inner housing (304C) shows tabs (412) transversely extending from proximal surface (414) of inner housing (304C). FIG. 13 shows a distal view of inner housing (304B) when tray (416) is removed from tray spaces of inner housing (304B), along with plug (418), bulk chamber cap (420), outer cup (303), and gear shaft (422). One way that inner housing (304C) differs from inner housing (304A) is that inner housing (304C) includes two tissue sample or tray receiving chambers (345C) and a plug chamber (424) along with bulk chamber (308) rather than a single tray receiving chamber along with bulk chamber (308).

Figure 16:
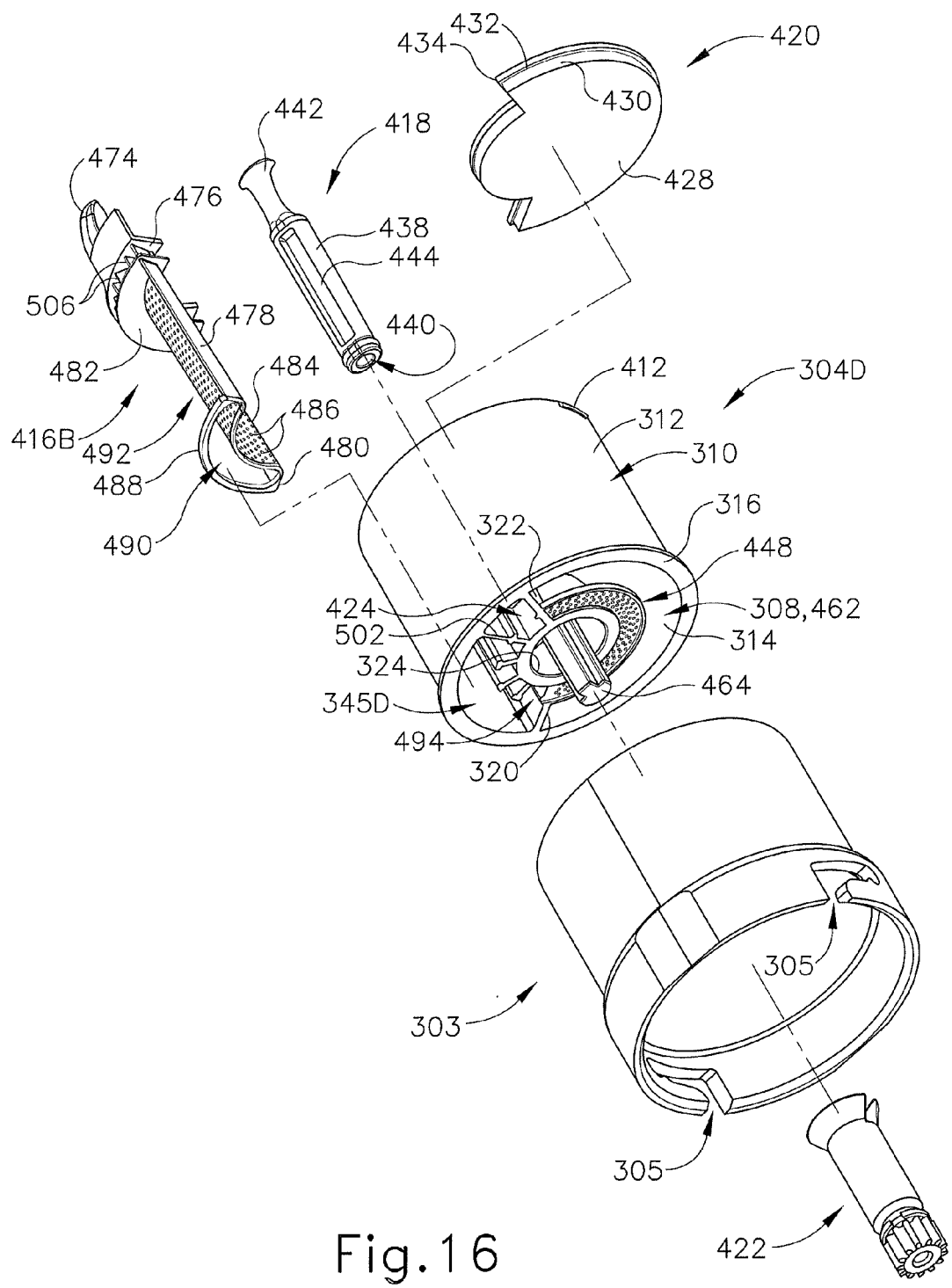
FIG. 16 is an exploded view of the tissue sample holder of FIG. 3, showing the inner housing of FIG. 16, a single prong tray, a marker and/or medication seal plug, a bulk chamber cap, a gear shaft, and an outer cup.

Bulk chamber cap (420) is configured to correspond with a shape of bulk chamber (308) to seal bulk chamber (308). Bulk chamber cap (420) includes a recessed portion having a corresponding shape with a profile defined by walls (320, 322, 324). Cap (420) includes proximal surface (426) (FIG. 14) and distal surface (428) (FIG. 13) and three walls (430, 432, 434) disposed therebetween. As shown in FIG. 16, first longitudinal wall (430) extends from distal surface (428) to transverse wall (432). Transverse wall (432) transversely extends between first longitudinal wall (430) and second longitudinal wall (434). Second longitudinal wall (434) extends from proximal surface (426) of cap (420). First longitudinal wall (430) is shaped to abut interior wall face (314) of inner housing (304C) and exterior faces of walls (320, 322, 324). Transverse wall (432) of cap (420) is shaped to abut portions of proximal surface (414) of inner housing (304C) and tabs (412). When cap (420) is disposed over inner housing (304C), cap (420) may connect to inner housing (304C) in a frictional fit connection, for example, between first vertical wall (430) of cap (420), interior wall face (314) of inner housing (304C), and exterior faces of walls (320, 322, 324). By longitudinal wall (432) of cap (420) extending and being disposed over tabs (412), the removal of cap (420) may be facilitated by allowing for a space under a portion of longitudinal wall (432) of cap (420) when cap (420) is seated to inner housing (304C) such that force sufficient to lift cap (420) from inner housing (304C) may be applied to the exposed portion of horizontal wall (432). FIG. 14 shows a view of cap (420) seated against inner housing (304C) when tissue sample holder (300) is assembled to include cap (420), inner housing (304C), outer cup (303), and gear shaft (422).

Proximal surface (426) of cap (420) includes handle (436) (FIG. 14), which allows for assistance with seating or removing cap (420) from inner housing (304C). Handle (436) may also be used to facilitate manual rotation of inner housing (304C) within outer cup (303) in versions where inner housing (304C) is manually rotatable. In the present example, however, rotation of inner housing (304C) is provided by motor (301) via shaft (422). As with the rotation described above for the first tissue sample holder version, inner housing (304C) may be rotated until one of tissue sample chambers (345C) of FIG. 12 is disposed over port (306) as shown in FIG. 5, such that tissue samples may be received within the selected tissue sample chamber (345C). Alternatively, inner housing (304C) may be rotated until plug chamber (424) is disposed over the sample entry point to deliver an item or material, such as a marker and/or a medication, via delivery means such as a marker deployer, which may be constructed and operable in accordance with the teachings of U.S. Patent App. Pub. No. 2009/0209854, entitled "Biopsy Method", published Aug. 20, 2009, the disclosure of which is incorporated by reference herein. Plug (418) is configured for receipt within plug chamber (424) when a marker or medication is not being deployed by a deployer, as described above, and acts to seal plug chamber (424) while tissue sample is received in one of tissue sample chambers (345C). Plug (418) includes post (438) having aperture (440) extending therethrough and handle (442) disposed at a proximal end of post (438). Post (438) of plug (418) defines elongated slot (444), which may be open to aperture (440) or which may restrict access to aperture (440) via a slot door.

Referring back to FIG. 12, inner housing (304C) includes tissue sample chambers (345C), plug chamber (424), and bulk chamber (308). Tissue sample chambers (345C) and plug chamber (424) are separated from bulk chamber (308) by walls (320, 322, 324). Walls (320, 322) project inwardly from interior wall face (314) of outer annular wall (310) of inner housing (304A), and wall (324) is disposed between end portions of walls (320, 322). While wall (324) is shown as arcuately shaped, wall (324) may be formed to include other shapes apparent to those of ordinary skill in the art.

Inner housing (304C) of the present example further includes interior walls (372, 374) disposed between inwardly extending walls (320, 322) and extending between interior wall face (314) of outer annular wall (310) and centrally disposed wall (324) to define two tissue sample chamber (345B) and plug chamber (424). While two tissue sample chambers are shown in this example, more or fewer interior walls may be included to define a greater or fewer number of tissue sample chambers, respectively. Additionally, while a single plug chamber is shown in this example, more interior walls may be included to define a greater number of plug chambers as desired. And while the tissue sample chambers are illustrated to have a generally trapezoidal shape and the plug chamber is illustrated as having an annular shape, other shapes, sizes, and configurations for the chambers are within the scope of this disclosure.

As an alternative to a third tissue sample chamber (345B) of inner housing (304B), inner housing (304C) includes annular plug chamber (424) defined by an opposite face of interior wall (374), interior faces of walls (322, 324), and third portion (P3) of interior wall face (314).

The proximal portion of centrally disposed wall (324) is disposed between proximal portions of walls (320, 322) and a distal portion of wall (324) includes transversely extending ledge (445) from which three extensions (450) distally project and extend towards floor (446) of central piece (448). Floor (446) transversely extends from wall (324) and extensions (450) of wall (324). Floor (446) includes edges (452) demarcating an area indicating a line of separation between proximal and distal portions of walls (320, 322), respectively. Floor (446) includes an annular portion (454) projecting from edges (452). Annular ramp wall (456) distally projects from annular portion (454) of floor (446) along distal portions of walls (320, 322) to sump floor (458), which includes apertures (460) through which fluids or liquid may be suctioned through and removed from inner housing (304C).

Lower, distal portions of walls (320, 322), fourth portion (P4) of interior wall face (314) of inner housing (304C), and an outer edge of sump floor (458) define space (462) through which tissue sample may be received into bulk chamber (308). Post (464) projects from a distal surface of floor (446), as shown in FIG. 13. Post (464) is sized for receipt into a proximal aperture (not shown) of gear shaft (422). The proximal aperture is shaped and sized to receive post (464) in a keyed relationship. The keyed relationship allows rotation of gear shaft (422) to rotate post (464), which in turn rotates inner housing (304C) within outer cup (303). The rotation is effected by shaft (422) meshing with a component of rotation mechanism (302) driven by motor (301). Of course, rotation may alternatively be provided in any other suitable fashion by any other suitable components/techniques.

As shown in FIG. 13 and similar to the second version shown in FIG. 10, interior faces of inwardly projecting walls (320, 322) as well as the faces of interior walls (372, 374) each include front portion (F), rear portion (R), and an elongated protrusion (336) internally extending from the upper portion of each of the walls. Elongated protrusions (336), the rear portions of walls (320, 372, 374), and interior wall face (314) of outer annular wall (310) together define a distal end of two separate tray space cavities (466, 468) for receiving and retaining two respective prongs (470, 472) of removable tray (416A), respectively, as described below. As shown in FIG. 12, opposite proximal end of tray space cavities (466, 468) respectively receive prongs (470, 472) of removable tray (416) (FIG. 13). The proximal end of tray space cavities (466, 468) is defined by the rear portions of walls (320, 372, 374), first and second portions (P1 and P2) of interior wall face (314) of outer annular wall (310), and the interior face of the upper portion of centrally disposed wall (324).

Tray (416A), as shown in FIG. 13, includes handle (474) proximally extending from arcuate and elongate proximal end wall (476). Outer tray walls (478, 480) of first prong (470) and of second prong (472) each project distally from an underside of proximal end wall (476). Arcuate walls (482) are disposed distal of and proximate to proximal end wall (476) for each of the prongs. External peripheral ends of proximal end wall (476) and arcuate walls (482) act as wiper seals providing an additional seal between the proximal end of tray (416A) and tissue sample chambers (345C) when the prongs (470, 472) of tray (416A) are respectively received in tray space cavities (466, 468) defined by walls of tissue sample chambers (345C) to prevent potential seepage of tissue sample liquid or the tissue sample; and also help to maintain a vacuum within chambers (345C). The peripheral ends may, for example, form a frictional fit with the walls tray space cavities (466, 468) of inner housing (304C). Tray (416A) and/or other components of tissue sample holder (300) may also include face seals and/or various types of elastomers to create a seal.

Floors (484) are disposed between each set of outer tray walls (478, 480) and include apertures (486). Each of the prongs includes base end wall (488) extending from a respective floor (484) at a distal end. Each base end wall (488) is disposed between ends of respective outer tray walls (478, 480). Base end walls (488) are each sized for reception within respective tray space cavities (466, 468). Base end walls (488) each include internal walls defining aperture (490) through which a tissue sample may be received from, for example, cutter (200) as described above. For each prong, floor (484), outer tray walls (478, 480), an underside of arcuate wall (482), and a proximal surface of base end wall (488) define a tissue sample receiving space (492). Apertures (486) of arcuately shaped floor (484) are sized in a manner similar to that described above for apertures (358) of the first version. Similarly, fluids from a tissue sample received in tissue sample receiving spaces (492) via port (306) of probe (100) may flow through apertures (486) to respective fluid receiving spaces (494) while the tissue sample remains in a respective prong of tray (416) positioned within a respective tray space. Fluid receiving spaces (494) are formed, as shown in FIG. 13, by front portions (F) of the interior face of walls (322, 372, 374), elongate protrusions (336), an underside of ledge (445), the interior face of extensions (450) of the distal portion of centrally disposed wall (324), and floor (484) of prongs (470, 472) of tray (416A). The fluid may then flow back through biopsy device (10) via vacuum port (307) as described above through to tubes connected to vacuum source (800).

VII. Exemplary Fourth Version of an Inner Housing for a Tissue Sample Holder

Figure 15:
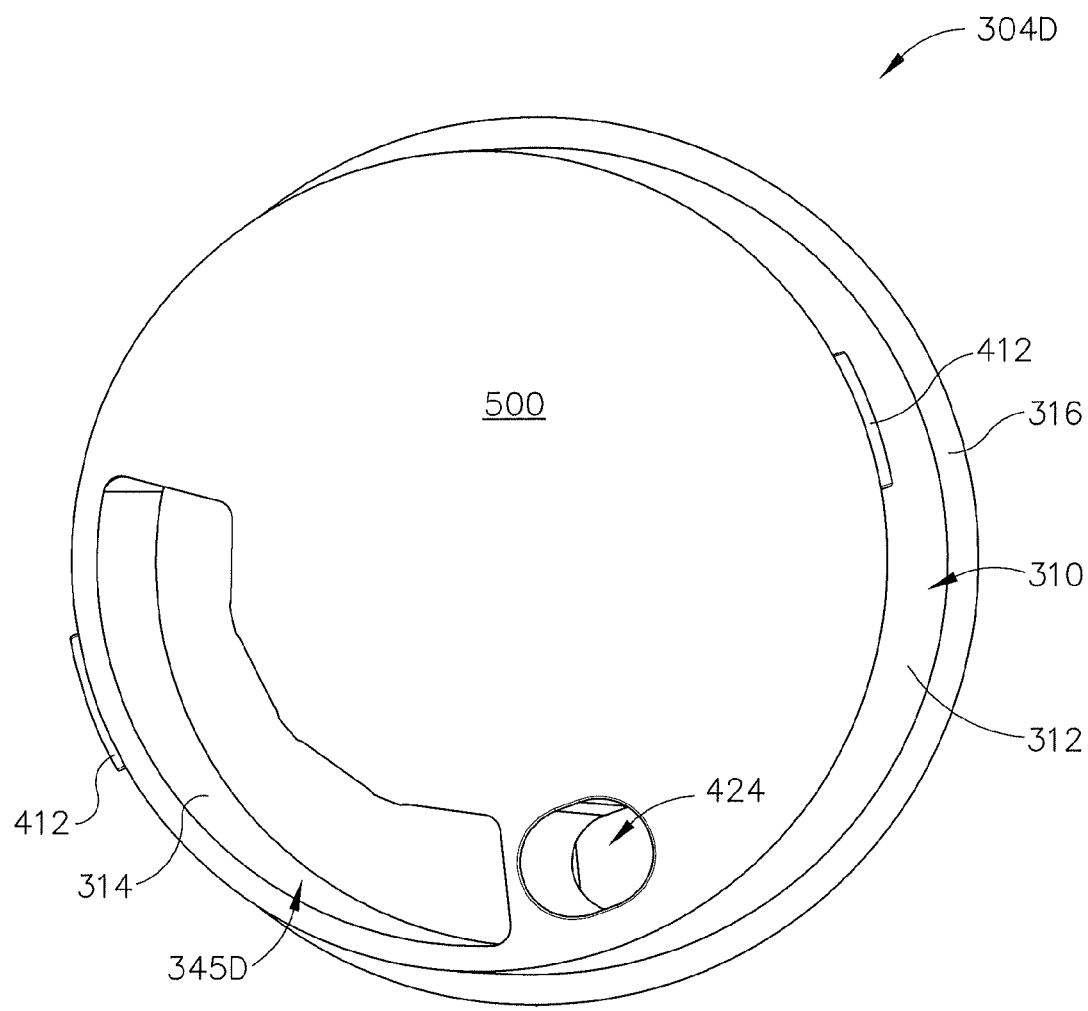
FIG. 15 is a perspective view of the proximal end of another example of an inner housing for the tissue sample holder of FIG. 3.

FIGS. 15-16 show another exemplary version of inner housing (304D) for tissue sample holder (300) of biopsy device (10). The reference numbers used for like components of inner housings (304A, 304B, 304C) are also used for inner housing (304D). Further, the similarities between the versions herein will generally not be further discussed.

Inner housing (304D) differs from the inner housing (304C) in that inner housing (304D) includes a single tissue sample chamber (345D) along with plug chamber (424) rather than multiple tissue sample chambers. Inner housing (304D) may include a proximal surface seated to cap (420) in a manner similar to that described for inner housing (304C). FIG. 15 shows an alternative proximal surface of inner housing (304D) in which bulk chamber (308) is sealed by upper floor (500) disposed within an upper periphery of outer annular wall (310) of inner housing (304D) such that tissue sample chamber (345D) and plug chamber (424) are in communication with apertures defined in upper floor (500).

FIG. 16 shows a distal end of inner housing (304D). Walls (320, 502) define tissue sample chamber (345D) along with a first portion of interior wall face (314) of outer annular wall (310). Walls (322, 502) define plug chamber (424) along with a second portion of interior wall face (314) of outer annular wall (310). Ribs (504) extend from an interior face of wall (324) towards the first portion of interior wall face (314) to a length sufficient to abut floor (484) of tray (416B) when tray (416B) is received within the rear portion of tissue sample chamber (345D) in a manner similar to that described above for the fourth version. Additionally, tray (416B) is similar to tray (416A) described above for the fourth version except that tray (416B) includes a single prong rather than two prongs and includes a plurality of bins (506) disposed between end wall (476) and arcuate wall (482). Further, tissue sample receiving space (492) for tray (416B) is sized to receive several tissue samples while each tissue sample receiving space (492) for tray (416A) was sized for receipt of only a single tissue sample.

VIII. Exemplary Fifth Version of an Inner Housing for a Tissue Sample Holder

Figure 17:
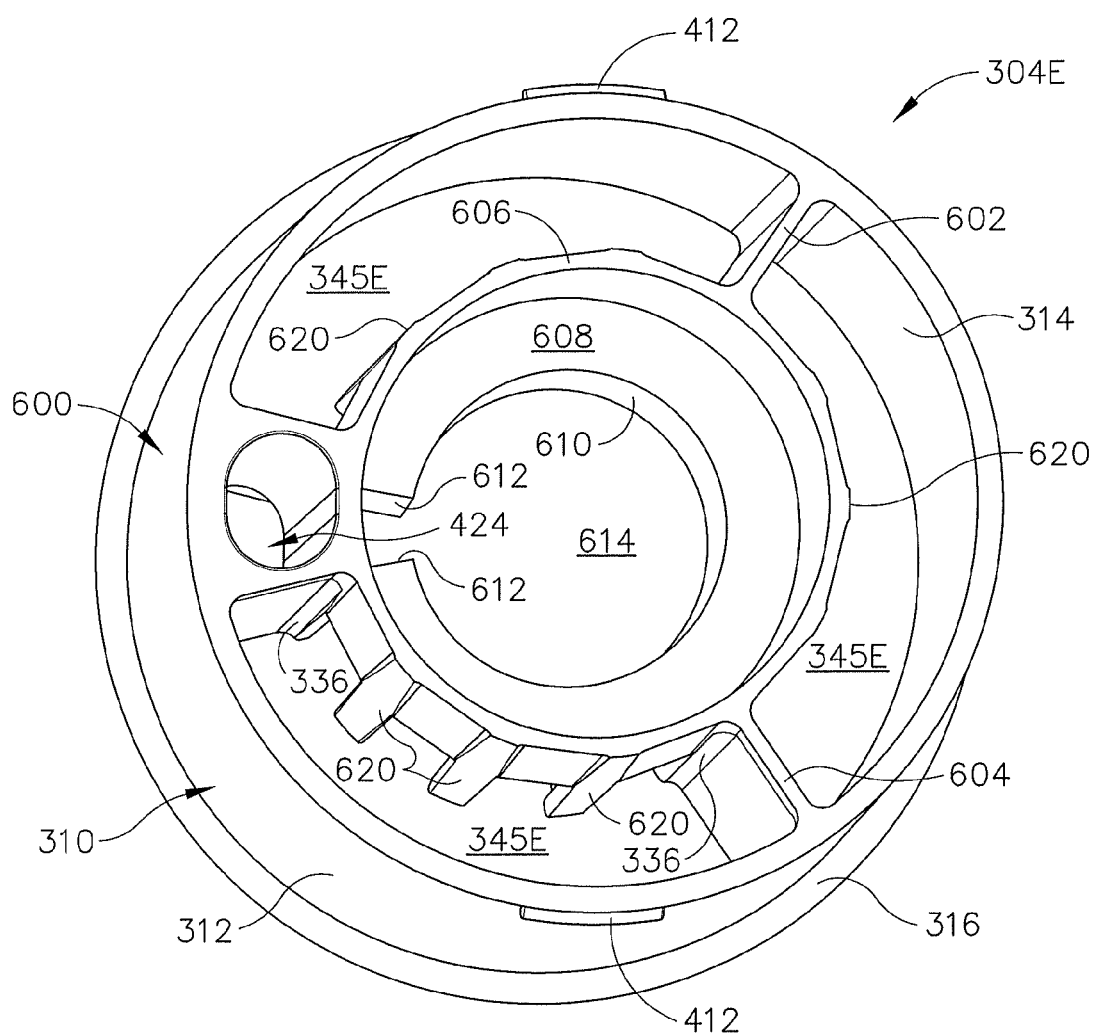
FIG. 17 is a perspective view of the proximal end of another example of an inner housing for the tissue sample holder of FIG. 3.
Figure 18:
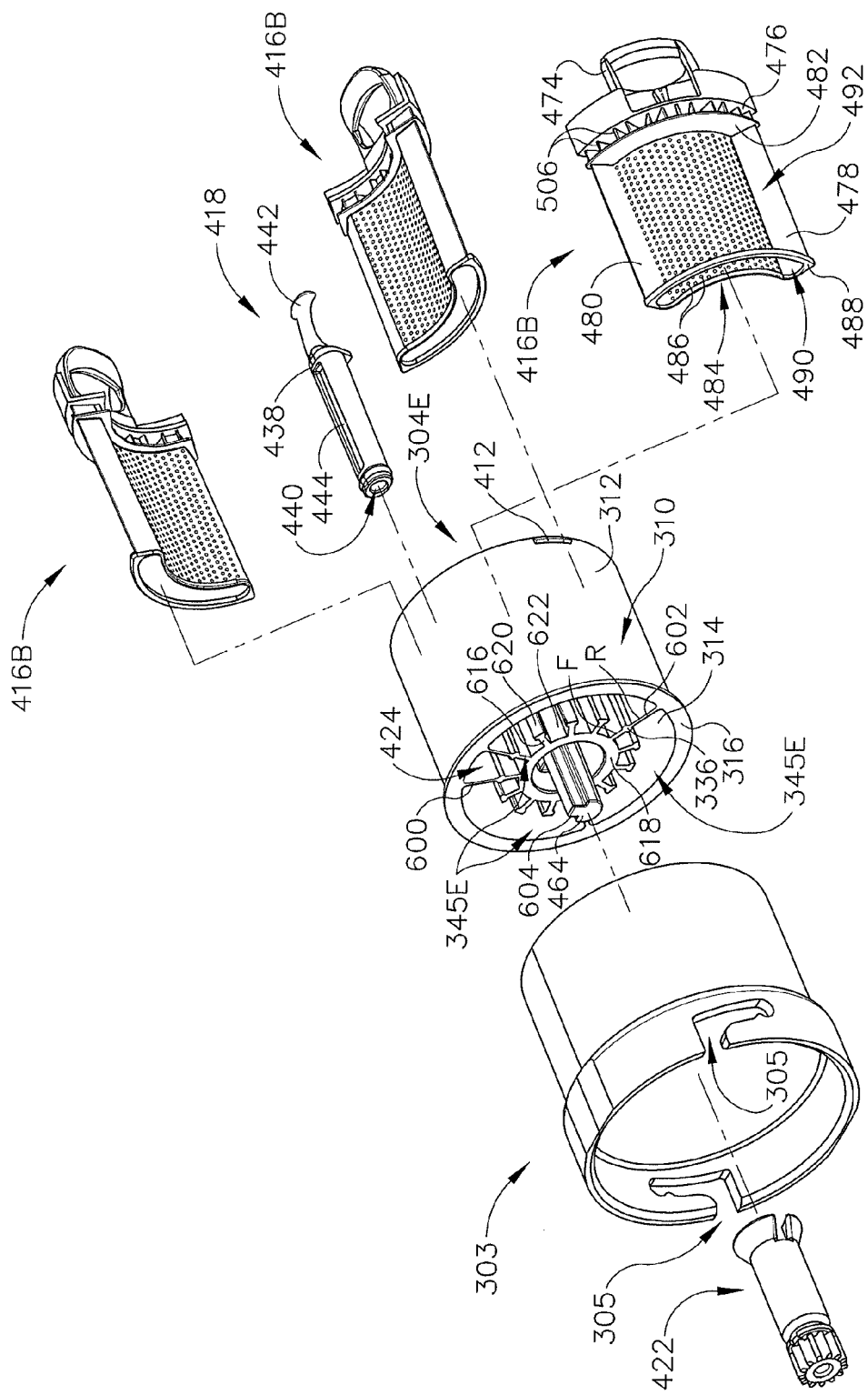
FIG. 18 is an exploded view of the tissue sample holder of FIG. 3, showing the inner housing of FIG. 17, a plurality of single-prong trays, a marker and/or medication seal plug, a bulk chamber cap, and a gear shaft.

FIGS. 17-18 show another exemplary version of inner housing (304E) for tissue sample holder (300) of biopsy device (10). The reference numbers used for like components of inner housings (304A, 304B, 304C. 304D) previous versions are also used for inner housing (304E). Further, the similarities between the versions herein will generally not be further discussed.

Inner housing (304E) includes tray receiving chambers (345E), or tissue sample chambers, that are configured to receive trays (416B). Trays (416B) are similar to the single-prong tray (416B) received in inner housing (304D) and generally will not be discussed further.

Referring to FIG. 17, plug chamber (424) is defined at a proximal end within wall (600) that is disposed between first and second tissue sample chambers (345E). A third tissue sample chamber (345E) is disposed between and separated from first and second tissue sample chambers (345E) via walls (602, 604). Each of walls (600, 602, 604) extend between interior annular wall (606) and outer annular wall (310). Ledge (608) transversely extends from a central portion of interior annular wall (606) and includes distally extending annular extension (610) and vertical extensions (612) that extend to floor (614). Similar to the fourth version, and as shown in FIG. 18, post (464) distally projects from floor (614). Referring to FIG. 18 showing a distal view of inner housing (304E), tissue sample chambers (345E) and plug chamber (424) include front portions (F) and rear portions (R). Distal ends of walls (600, 602, 604) include protrusions (336) as described above within previous versions. Vertical ribs (616) project from interior annular base (618) towards interior wall face (314) of outer annular wall (310) to a distance similar to the distance protrusion (336) is positioned on a respective wall with respect to interior annular base (618). Ribs (616) include a T-shaped profile such that an inside portion vertically extends from interior annular base (618) disposed below floor (614) and an end portion adjacent the inside portion has a width greater than the width of the inside portion. Referring back to FIG. 17, end portions of ribs (616) extend distally from projections (620) disposed on interior annular wall (606). Spaces defined by ribs (616), an underside of ledge (608), and annular base wall (622) extending between interior annular base (618) and floor (614), as well as spaces defined by walls (600, 602, 604), an underside of ledge (608), and at least one rib (616), are fluid receiving spaces (494) that operate in a manner as described above for fluid receiving spaces of previous examples.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A tissue sample holder configured to engage a biopsy probe and receive a tissue sample, the tissue sample holder comprising:
   (a) a housing including at least a first chamber and a second chamber, wherein the first chamber has a first volume, wherein the second chamber has a second volume, wherein the chambers each extend along an axial direction parallel to a rotational axis of a cutter associated with the biopsy probe, wherein the first chamber extends along a first angular extent and the second chamber extends along a second angular extent, wherein the first angular extent is greater than the second angular extent, wherein the housing is rotatable to successively index the chambers with the cutter, and wherein the first volume is greater than the second volume; and
   (b) at least one tray, wherein the tray is configured to be axially received within at least one of the chambers, wherein the at least one tray is configured to receive a tissue sample, wherein the housing is configured to receive suction such that excess liquid received within the chambers is redirected away from the tissue sample contained therein.

2. The tissue sample holder of claim 1, wherein the housing further includes:
   (i) an outer member having a proximal edge and a distal edge, wherein the outer member defines a central bore,
   (ii) a plurality of radially extending walls extending from the outer member, and
   (iii) an inner member extending between inner ends of the plurality of radially extending walls, the inner ends spaced from the outer member, wherein the outer member, the inner member, and the walls define at least one of the at least two tissue sample chambers;
   wherein a first portion of the outer member, the inner member, a first outer wall of the plurality of walls, and a second outer wall of the plurality of walls define the first chamber,
   wherein a second portion of the outer member, the inner member, and at least two of the walls of the plurality of walls define the second chamber, and
   wherein the first chamber is separate from the second chamber.

3. The tissue sample holder of claim 2 wherein each chamber of the chambers includes a proximal end and a distal end, wherein the proximal end is configured to receive a tray, wherein the distal end is configured to be positioned proximate to the probe, wherein the plurality of radially extending walls in the housing extend between the proximal end and the distal end.

4. The tissue sample holder of claim 2, wherein the at least one tray includes:
   (i) a pair of sidewalls, each sidewall having a proximal edge and a distal edge,
   (ii) a base end wall engaged with the sidewalls, the base end wall having a proximal edge and a distal edge, the base end wall defining an aperture, and (iii) a floor coupled to the proximal edges of the sidewalls and the proximal edge of the base end wall;

wherein the tray is configured to be received within a chamber of the first chamber or the second chamber and the distal edges of the sidewalls of the tray are configured for receipt into the respective chamber.

5. The tissue sample holder of claim 4, wherein the floor of each tray includes a plurality of openings, wherein the openings are sized to block tissue.

6. The tissue sample holder of claim 1, further including an outer cup and a detachable cap, wherein the detachable cap is configured to fasten to the outer cup, wherein the outer cup is configured to receive the housing.

7. The tissue sample holder of claim 1, further including a central member, wherein the central member is associated with at least one of the first chamber or the second chamber of the housing.

8. The tissue sample holder of claim 7, wherein the central member includes a plurality of openings, wherein the plurality of openings are configured to permit fluid flow.

9. The tissue sample holder of claim 8, wherein the central member is associated with the second chamber.

10. The tissue sample holder of claim 9, wherein the central member is configured to receive fluid flowing out of the second chamber.

11. The tissue sample holder of claim 10, wherein the central member extends radially around a portion of the housing.

12. The tissue sample holder of claim 11, wherein the central member terminates at a radial point prior to the first chamber.

13. The tissue sample holder of claim 7, wherein the central member extends outwardly relative to a central axis defined by the housing.

14. The tissue sample holder of claim 7, wherein the housing encompasses the central member.

15. A tissue sample holder configured to associate with a biopsy probe and receive a tissue sample severed by a cutter of the biopsy probe, the tissue sample holder comprising:
(a) a housing including at least a first tissue sample chamber and a second tissue sample chamber, wherein the tissue sample chambers each extend along an axial direction parallel with a cutter lumen defined by a portion of the biopsy probe, wherein the first tissue sample chamber extends along a first angular extent, wherein the second tissue sample chamber extends along a second angular extent, wherein the first angular extent is greater than the second angular extent, wherein the first tissue sample chamber defines a first volume, the second tissue sample chamber defines a second volume, wherein the second tissue sample chamber is angularly adjacent to the first tissue sample chamber in a circumferential direction, and wherein the first volume is greater than the second volume, wherein the housing is configured to be suctioned such that fluids are removed from the first and second tissue sample chambers; and
(b) at least one tray, wherein the tray is configured to be axially received within at least one of the tissue sample chambers, wherein the at least one tray is configured to receive a tissue sample.

16. The tissue sample holder of claim 15, wherein the housing further includes:

(i) an outer member having a proximal edge and a distal edge, wherein the outer member defines a central bore,
(ii) a plurality of radially extending walls extending from the outer member, and
(iii) an inner member extending between inner ends of the plurality of radially extending walls, the inner ends spaced from the outer member, wherein the outer member, the inner member, and the walls define at least one of the tissue sample chambers;

wherein a first portion of the outer member, the inner member, a first outer wall of the plurality of walls, and a second outer wall of the plurality of walls define the first tissue sample chamber, wherein a second portion of the outer member, the inner member, and at least two of the walls of the plurality of walls define the second tissue sample chamber, and wherein the first tissue sample chamber is separate from the second tissue sample chamber.

17. The tissue sample holder of claim 16, wherein a distal end of the housing is configured to be positioned proximate to the probe, wherein the plurality of radially extending walls in the housing extend between a proximal end and the distal end.

18. The tissue sample holder of claim 16, wherein the at least one tray includes:
(i) a pair of sidewalls,
(ii) a base end wall, and
(iii) a floor, wherein the floor is coupled to the pair of sidewalls and the base end wall to define a tissue receiving recess;

wherein the at least one tray is configured to be received within a chamber of the at least two tissue sample chambers.

19. A tissue sample holder of claim 18, wherein the at least one tray includes two trays.

20. A tissue sample holder configured to engage a biopsy probe and receive a tissue sample, the tissue sample holder comprising:
(a) a housing including an outer wall that defines a circumference, wherein the outer wall includes a first portion and a second portion, wherein the first portion defines a bulk chamber with a first angular extent, wherein the second portion defines at least one tray receiving chamber with a second angular extent that is less than the first angular extent, wherein the bulk chamber defines a first volume, wherein the tray receiving chamber defines a second volume, wherein the first volume is greater than the second volume, wherein the first and second angular extents together form a portion of the circumference; and
(b) at least one tray, wherein the tray is configured to be axially received within the tray receiving chamber parallel to an insertion axis defined by the biopsy probe, wherein the at least one tray is configured to receive a tissue sample, wherein the bulk chamber is configured to receive a greater quantity of tissue samples than the tray receiving chamber, wherein the housing is in communication with a vacuum source such that at least a portion of the housing is configured to extract excess fluids from the chambers.

* * * * *